United States Patent
Hong et al.

(10) Patent No.: US 10,544,119 B2
(45) Date of Patent: Jan. 28, 2020

(54) PREPARATION METHOD FOR CHIRAL INTERMEDIATE FOR USE IN STATINS

(71) Applicants: Asymchem Laboratories (Tianjin) Co., Ltd., Tianjin (CN); Asymchem Life Science (Tianjin) Co., Ltd., Tianjin (CN); Tianjin Asymchem Pharmaceutical Co., Ltd., Tianjin (CN); Asymchem Laboratories (Fuxin) Co., Ltd., Fuxin (CN); Jilin Asymchem Laboratories Co., Ltd., Dunhua (CN)

(72) Inventors: Hao Hong, Tianjin (CN); Chaoyong Chen, Tianjin (CN); Jiuyuan Li, Tianjin (CN); Litao Shen, Tianjin (CN); Lina Guo, Tianjin (CN); Hongying Tian, Tianjin (CN)

(73) Assignees: Asymchem Laboratories (Tianjin) Co., Ltd., Tianjin (CN); Asymchem Life Science (Tianjin) Co. Ltd., Tianjin (CN); Tianjin Asymchem Pharmaceutical Co., Ltd., Tianjin (CN); Asymchem Laboratories (Fuxin) Co., Ltd., Liaoning (CN); Jilin Asymchem Laboratories Co., Ltd., Jilin (CN)

( * ) Notice: Subject to any disclaimer, the term of this patent is extended or adjusted under 35 U.S.C. 154(b) by 452 days.

(21) Appl. No.: 15/309,469

(22) PCT Filed: Aug. 4, 2014

(86) PCT No.: PCT/CN2014/083636
§ 371 (c)(1),
(2) Date: Nov. 8, 2016

(87) PCT Pub. No.: WO2015/168998
PCT Pub. Date: Nov. 12, 2015

(65) Prior Publication Data
US 2017/0190684 A1    Jul. 6, 2017

(30) Foreign Application Priority Data
May 9, 2014    (CN) .......................... 2014 1 0195360

(51) Int. Cl.
*C07D 319/06*    (2006.01)
*C12P 7/62*    (2006.01)
*C07C 51/367*    (2006.01)
*C07C 67/30*    (2006.01)
*C07C 67/313*    (2006.01)

(52) U.S. Cl.
CPC .......... *C07D 319/06* (2013.01); *C07C 51/367* (2013.01); *C07C 67/30* (2013.01); *C07C 67/313* (2013.01); *C12P 7/62* (2013.01)

(58) Field of Classification Search
None
See application file for complete search history.

(56) References Cited

U.S. PATENT DOCUMENTS

2006/0004200 A1    1/2006    Gudipati et al.

FOREIGN PATENT DOCUMENTS

| JP | 06107592 A | 4/1994 |
| JP | 2006514079 A | 4/2006 |

OTHER PUBLICATIONS

Wu X et al. Preparation of ethyl 3R,5S-6-(benzyloxy)-3,5-dihydroxy-hexanoate by recombinant diketoreductase in a biphasic system. 2011. Bioresource Technology. 102:3649-3652. (Year: 2011).*
Wu et al., "Enantioselective synthesis of ethyl (2)-2-hydroxy-4-phenylbutyrate by recombinant diketoreductase," Tetrahedron Asymmetry (Nov. 4, 2009); 20(21):2504-2509.
Guo et al., "Synthesis of ethyl and t-butyl (3R,5S)-dihydroxy-6-benzyloxy hexanoates via diastereo- and enantioselective microbial eduction," Tetrahedron Asymmetry (Jun. 19, 2006); 71(10):1589-1602.
Minami et al., "Stereoselective reduction of beta, d-diketo esters derived from tartaric acid. A facile route to optically active 6-oxo-3,5-syn-isopropylidenedioxyhexamoate, a versatile synthetic intermediate of artificial HMG Co-A reductase inhibitors," Tetrahedron Letters (Dec. 31, 1993); 34:513-516.
Nahm et al., "N-Methoxy-N-Methylamides as Effective Acylating Agents," Tetrahedron Letters (1981); 22(39):3815-3818.
Hanamoto et al., "A Facile Entry to ß,ò-Diketo and syn-ßò-Dihydroxy Esters," Tetrahedron Letters (1988); 29(49):6467-6470.

(Continued)

*Primary Examiner* — Paul J Holland
(74) *Attorney, Agent, or Firm* — Fox Rothschild LLP

(57) ABSTRACT

The present invention relates to a preparation method for a chiral intermediate for use in statins, acquired with chloroacetic acid and benzyl alcohol as starting materials via a series of reactions, namely etherification, condensation, substitution, and asymmetric reduction. The preparation method provided in the present invention has a novel route of synthesis, allows an intermediate compound to be introduced conveniently into the chiral center of a glycol via enzyme reduction, and not only is low in costs, but also is reliable in quality. The route of synthesis provided in the present invention uses raw materials of low costs, has an easy to operate process, and provides a final product of great purity and high yield.

8 Claims, No Drawings
Specification includes a Sequence Listing.

(56) References Cited

OTHER PUBLICATIONS

Kürti et al., "Strategic Applications of Named Reactions in Organic Synthesis,".

Jackson et al., "An Unexpected Equilibrium Process Associated with a Standard Approach to Ynone Synthesis," JOC Note (2002):5032-5035.

* cited by examiner

PREPARATION METHOD FOR CHIRAL INTERMEDIATE FOR USE IN STATINS

CROSS-REFERENCE TO RELATED APPLICATIONS

The present application is the U.S. national phase of PCT application PCT/CN2014/083636, filed on Aug. 4, 2014 with the title "Preparation Method for Chiral Intermediate for Use in Statins", which claims priority from Chinese patent application No. 201410195360.1, filed on May 9, 2014 with the title "Preparation Method for Chiral Intermediate for Use in Statins". The disclosures of both applications are incorporated herein by reference.

TECHNICAL FIELD

The present invention relates to the field of synthesis of pharmaceutical intermediates, and specifically to a method for preparing a chiral intermediate for use in statin drugs.

BACKGROUND ART

Statin drugs are inhibitors of hydroxymethylglutaryl coenzyme A (HMG-CoA) reductase. This class of drugs block the metabolic pathway of intracellular mevalonic acid and reduce the intracellular cholesterol synthesis by competitively inhibiting the rate-limiting enzyme for endogenous cholesterol synthesis, HMG-CoA reductase, so as to increase the number and the activity of the low density lipoprotein (LDL) receptor on the surface of the feedback-stimulated cell membrane (mainly of hepatic cells), increase the clearance rate of serum cholesterol, and reduce the level thereof. Statin drugs can also inhibit the liver from synthesizing apolipoprotein B-100, so as to reduce the synthesis and secretion of triglyceride-riched AV and lipoprotein. In addition, early-stage application of statin drugs in patients suffered from acute coronary syndrome can inhibit the inflammatory response of the vascular endothelium, stabilize atherosclerotic plaque, improve the functions of the vascular endothelium; delay the degree of atherosclerosis (AS), and have anti-inflammatory, neuro-protective and anti-thrombosis effects. Accordingly, they have a very broad prospect of application.

The syntheses of currently marketed statin drugs, such as atorvastatin, pitavastatin, simvastatin, and rosuvastatin, all require using the chiral glycol side chain of formula A as a starting material.

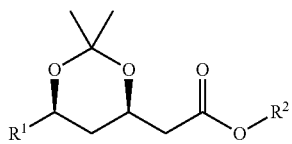

A

In patent application WO 03006656A, 2,4-dideoxy hexose or 2,4,6-trideoxy hexose is used as an important intermediate, which undergoes oxidation, acetalation and hydrolysis to give the alcoholic side chain intermediate.

Reaction Scheme 1

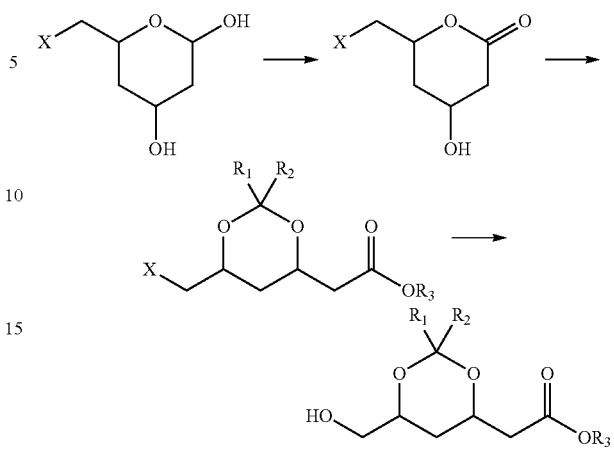

Patent application WO 0206266A reports a route for synthesizing a series of tert-butyl (4R-cis)-6-chloro-2,2-dimethyl-1,3-dioxane-4-acetate compounds from 6-chloromethyl-4-hydroxy tetrahydro-2H-pyran-2-one, wherein Y represents Na, Ca or a tetraalkylammonium.

Reaction Scheme 2

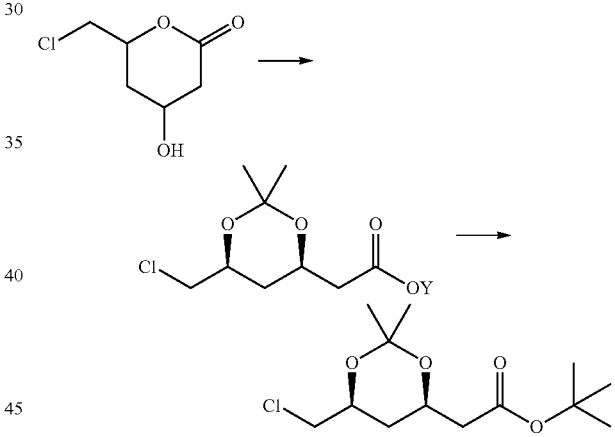

Patent applications US 2006004200A and WO 2008059519A report a synthetic process in which tert-butyl (4R-Cis)-6-hydroxymethyl-2,2-dimethyl-1,3-dioxane-4-acetate is oxidized to an aldehyde side chain intermediate.

Reaction Scheme 2

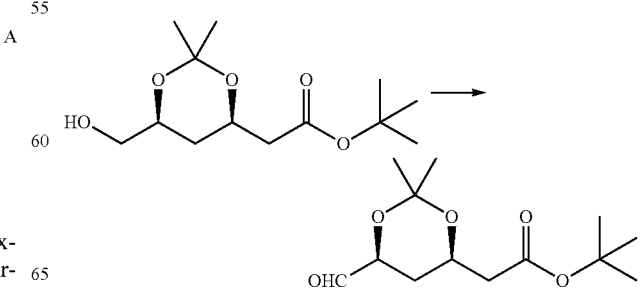

In the above routes, there are some problems in the aspects of synthesis of the starting materials, selection of the route, and separation and purification of the intermediates, which lead to high cost for synthesis and low overall yields. Therefore, developing a synthetic process with low-cost, environment friendliness and high product quality would have very high economic value and social value.

SUMMARY OF THE INVENTION

In order to overcome the problems of high costs and low yields in the existing synthetic routes, a totally new synthetic route is developed. One object of the present inventions is to provide a method for preparing a chiral intermediate of formula (I) for use in statin drugs.

The preparation method provided in the present invention comprises the following steps:

1) conducting etherification reaction using chloroacetic acid and benzyl alcohol as starting materials to produce benzyloxy acetic acid;
2) conducting condensation reaction of benzyloxy acetic acid with morpholine to produce 2-benzyloxymorpholine acetamide;
3) conducting substitution reaction of 2-benzyloxymorpholine acetamide with an acetylacetate ester of formula (5) to produce a diketone intermediate of formula (6);
4) conducting asymmetric reduction of the diketone intermediate of formula (6) to produce a chiral diol intermediate of formula (7);
5) reacting the chiral diol intermediate of formula (7) with 2,2-dimethoxypropane to produce (4R-cis)-6-(benzyloxy)-2,2-dimethyl-1,3-dioxane-4-hexanoate ester of formula (8);
6) removing the benzyl group from the (4R-cis)-6-(benzyloxy)-2,2-dimethyl-1,3-dioxane-4-hexanoate ester of formula (8) to give (4R-cis)-6-hydroxymethyl-2,2-dimethyl-1,3-dioxane-4-hexanoate ester of formula (9); and
7) conducting oxidation reaction of the (4R-cis)-6-hydroxymethyl-2,2-dimethyl-1,3-dioxane-4-hexanoate ester of formula (9) to give the chiral intermediate of formula (I).

The reaction scheme is as follows:

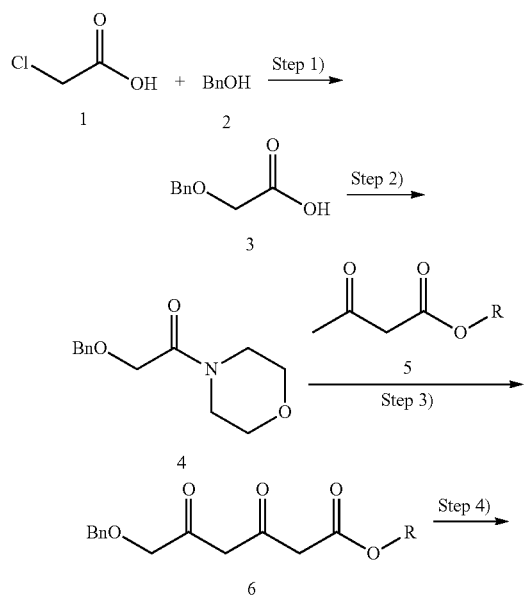

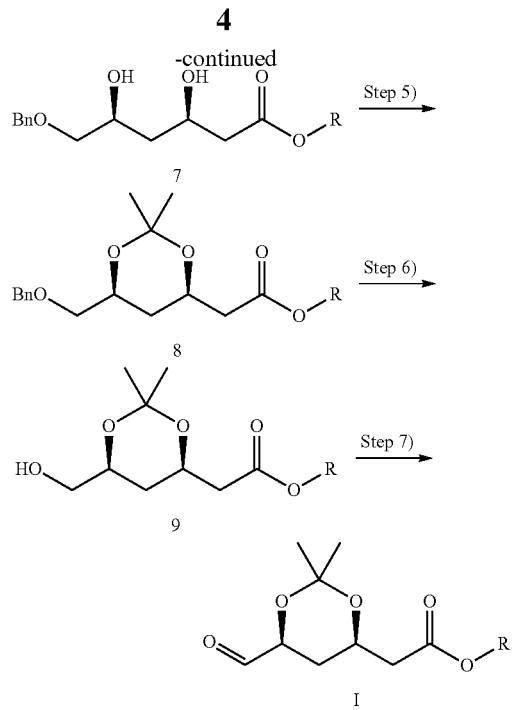

wherein R represents C4~C10 alkyl.

Preferably, R represents tert-butyl, tert-pentyl, cyclopentyl or cyclohexyl.

In one embodiment, the acetylacetate of formula (5) is prepared through ring opening addition reaction between diketen and an alcohol of formula (10).

The reaction scheme is as follows:

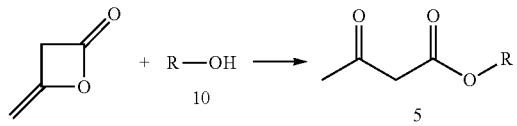

In one embodiment, the asymmetric reduction in step 4) comprises: evenly dispersing the diketone intermediate of formula (6) in a solvent, adding a reductase, formic acid or a formate salt, and $NAD^+$ (nicotinamide adenine dinucleotide), adjusting pH value to 6.2~6.4, then warming the system up to 27~33° C., and maintaining the temperature for 17~24 h.

In step 4), the mass ratio of the reductase to the diketone intermediate of formula (6) is 0.00005~0.004:1.

In one embodiment, the reductase is a diketoreductase mutant comprising one of the amino acid sequences shown below:
a) SEQ ID NO: 1 to SEQ ID NO: 6;
b) a sequence having at least 70% identity to a sequence shown in a) and having improved diketoreductase activities; or
c) a sequence obtained by deleting, adding and/or replacing one or more amino acid residues in a sequence shown in a) and having improved diketoreductase activities,
wherein the sequence shown in b) is not a sequence shown in SEQ ID NO: 7.

Preferably, the diketoreductase mutant comprises an amino acid sequence shown in SEQ ID NO: 1, 2, 3, 4, 5 or 6.

In step 4), the solvent is one or more selected from the group consisting of purified water, polyethylene glycol, isopropanol, acetonitrile, tetrahydrofuran, ethanol, n-heptane, toluene, acetone, DMF and methanol.

In step 4), the formate salt is selected from the group consisting of ammonium formate, sodium formate and potassium formate, and the molar ratio of formic acid or formate salt to the diketone intermediate of formula (6) is 2~10:1.

In step 4), the mass ratio of $NAD^+$ to the diketone intermediate of formula (6) is 0.001~0.1:1.

The preparation method provided in the present invention has the following advantages.

(1) In comparison with existing synthetic routes, the present synthetic route is more novel, extending the field of the development of statin drugs.

(2) Diol chiral centers can be conveniently introduced into the intermediate compound 6 by enzymatic reduction, especially by the diketoreductase mutant provided in the present invention, which is not only inexpensive, but also reliable in quality, and the diol can be obtained with a high yield, good purity and high optical selectivity.

(3) The present synthetic route uses chloroacetic acid and benzyl alcohol as the starting materials. The starting materials used in the intermediate steps are inexpensive. The process is easy to operate. The final product has a good purity. The yield is high: the overall yield can reach 90.0%0/ or above. Accordingly, the manufacturing cost can be effectively reduced.

SPECIFIC EMBODIMENTS

In order to make the objects, the technical solutions and the advantages of the present application more clear, the technical solutions of exemplary embodiments of the present application will be further described hereinbelow.

The present invention provides a method for preparing a chiral intermediate of formula (I) for use in statin drugs, comprising the following steps:
1) conducting etherification reaction using chloroacetic acid 1 and benzyl alcohol 2 as starting materials to produce benzyloxy acetic acid 3;
2) conducting condensation reaction of benzyloxy acetic acid 3 with morpholine to produce 2-benzyloxymorpholine acetamide 4;
3) conducting substitution reaction of 2-benzyloxymorpholine acetamide 4 with an acetylacetate ester of formula (5) to produce a diketone intermediate of formula (6);
4) conducting asymmetric reduction of the diketone intermediate of formula (6) to produce a chiral diol intermediate of formula (7);
5) reacting the chiral diol intermediate of formula (7) with 2,2-dimethoxypropane to produce a (4R-cis)-6-(benzyloxy)-2,2-dimethyl-1,3-dioxane-4-hexanoate ester of formula (8);
6) removing the benzyl group from the (4R-cis)-6-(benzyloxy)-2,2-dimethyl-1,3-dioxane-4-hexanoate ester of formula (8) to give (4R-cis)-6-hydroxymethyl-2,2-dimethyl-1,3-dioxane-4-hexanoate ester of formula (9); and
7) conducting oxidation reaction of the (4R-cis)-6-hydroxymethyl-2,2-dimethyl-1,3-dioxane-4-hexanoate ester of formula (9) to give the chiral intermediate of formula (I).

The reaction scheme is as follows:

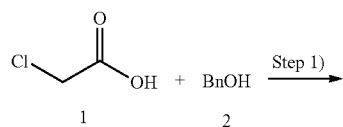

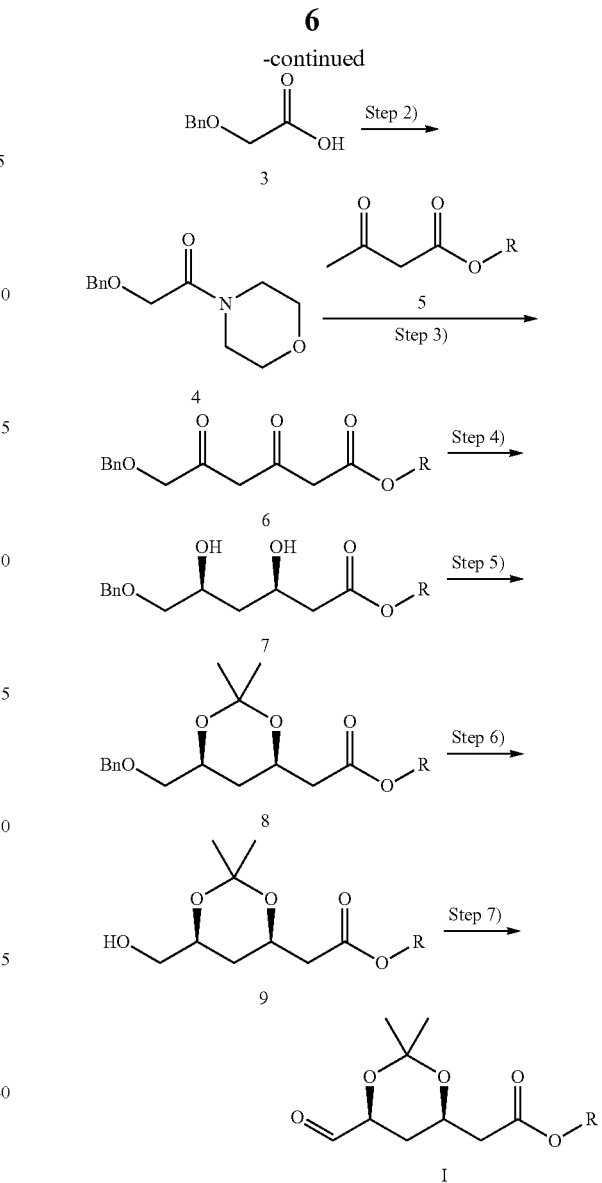

wherein R represents C4-C10 alkyl.

In one embodiment of the preparation method of the present invention, R preferably represents tert-butyl, tert-pentyl, cyclopentyl or cyclohexyl.

In one embodiment of the preparation method of the present invention, the acetylacetate of formula (5) is prepared through ring opening addition reaction between diketen and the alcohol of formula (10).

The reaction scheme is as follows:

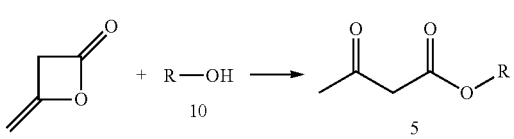

Specifically, the specific process of step 1) may comprise the followings. An organic solvent and toluene are added into a reaction flask, followed by adding an alkali in portions while controlling the temperature of the system, and adding benzyl alcohol in portions after the addition of the alkali is completed. Chloroacetic acid is dissolved in an organic solvent, and the resultant solution is added dropwise into the reaction system described above while controlling the temperature. The react is continued until chloroacetic acid is consumed completely. The system is cooled down, followed by adding water and removing the organic solvent under reduced pressure. The aqueous phase is extracted with an organic solvent. pH of the aqueous phase is adjusted to be acidic while controlling the temperature of the system. The aqueous phase is extracted with an organic solvent, and dried and concentrated to give the compound 3. The purity of the product obtained in step 1) is 97~99%, and the yield is 85~90%.

In the above step 1): the organic solvent used for reaction may be selected from the group consisting of 1,4-dioxane, tetrahydrofuran, 2-methyltetrahydrofuran, acetonitrile and methyl tert-butyl ether, or a mixture thereof in any ratio, preferably tetrahydrofuran; the added alkali may be selected from potassium carbonate, sodium carbonate, potassium hydroxide, potassium tert-butoxide, sodium ethoxide, sodium hydroxide, metallic sodium, sodium hydride, and a mixture thereof in any ratio, preferably potassium hydroxide; the molar ratio of the added alkali to chloroacetic acid may be 1:1~100:1, preferably 3:1; the molar ratio of the added benzyl alcohol to chloroacetic acid may be 1:1~100:1, preferably 3:1; the temperature at which the alkali and benzyl alcohol are added may be 10~100° C., preferably 15~25° C.; the temperature at which chloroacetic acid is added dropwise may be 30~120° C., preferably 70~80° C.; the rate at which the solution of chloroacetic acid is added dropwise may be from 1 g/min to 100 g/min, preferably 10 g/min; the mass ratio of water to chloroacetic acid which are added after cooling down may be 1:1~100:1, preferably 8:1; the pH value of the aqueous phase may be 1~6, preferably 2~3; the solvent for extracting the acidic aqueous phase may be selected from the group consisting of 2-methyl, ethyl acetate, diethyl ether, methyl tert-butyl ether, and a mixture thereof in any ratio, preferably methyl tert-butyl ether; and the volume of the solvent used for extraction may be 3~30 times, preferably 8 times, relative to the volume of chloroacetic acid.

The specific process of step 2) may comprise the followings. An organic solvent and benzyloxyacetic acid (compound 3) are added into a reaction flask, followed by adding dropwise an acyl chloride while controlling the temperature of the system. After the addition is completed, the system is stirred until compound 3 is completely consumed. Low boiling-point substances are then removed under reduced pressure, and the concentrated liquid is stored for further use. An organic solvent, morpholine and an alkali are added into a reaction flask, followed by adding dropwise the concentrated liquid obtained above while controlling the temperature of the system. After the addition is completed, the system is stirred while maintaining the temperature until morpholine is completely consumed. Diluted hydrochloric acid is added to quench the reaction. The liquid is separated, and the organic phase is washed sequentially with water, saturated sodium bicarbonate solution and water, and concentrated to give benzyloxyethylmorpholine amide (compound 4). The purity of the product obtained in step 2) is 97~99%, and the yield is 85~90%.

In the above step 2): the organic solvent may be selected from the group consisting of 1,4-dioxane, tetrahydrofuran, toluene, dichloromethane, chloroform, 2-methyltetrahydrofuran, acetonitrile, methyl tert-butyl ether, and a mixture thereof in any ratio, preferably dichloromethane; the added acyl chloride may be selected from the group consisting of oxalyl chloride, thionyl chloride, acetyl chloride, and a mixture thereof in any ratio, preferably oxalyl chloride; the temperature at which the acyl chloride is added dropwise may be −10~50° C., preferably 10~20° C.; the molar ratio of the added acyl chloride to compound 3 may be 1:1~10:1, preferably 1.5:1; the rate at which the solution of the acyl chloride is added dropwise may be from 1 g/min to 100 g/min, preferably 6 g/min; the added alkali may be selected from the group consisting of sodium hydroxide, triethylamine, sodium carbonate, potassium carbonate, potassium hydroxide, potassium tert-butoxide, sodium ethoxide, diisopropylethylamine, pyridine, and a mixture thereof in any ratio, preferably triethylamine; the molar ratio of the added alkali to compound 3 may be 1:1~10:1, preferably 1.5:1; and the temperature at which the concentrated liquid is added dropwise may be −10~50° C., preferably 10~20° C.

The specific process of step 3) may comprise the followings. An organic solvent and an alkali are added into a reaction flask, followed by adding compound 5 dropwise while controlling the temperature of the system. After the addition is completed, the system is cooled down, followed by adding dropwise a solution of an organic base while controlling the temperature of the system. After the addition is completed, compound 4 is added dropwise and the system is stirred until compound 4 is completely consumed. The reaction system is quenched with an acidic aqueous solution. The liquid is separated, and the aqueous phase is extracted twice with an organic solvent. The organic phase is combined, washed once with saturated brine, and concentrated to give crude compound 6, to which an organic solvent is added for crystallization to give solid compound 6. The purity of the product obtained in step 3) is 96.0~97.0%, and the yield is 65~70%.

In the above step 3): the organic solvent may be selected from the group consisting of 1,4-dioxane, tetrahydrofuran, toluene, 2-methyltetrahydrofuran, methyl tert-butyl ether, and a mixture thereof in any ratio, preferably tetrahydrofuran; the alkali used may be selected from the group consisting of potassium carbonate, sodium carbonate, potassium hydroxide, potassium tert-butoxide, sodium ethoxide, sodium hydroxide, metallic sodium, sodium hydride, and a mixture thereof in any ratio, preferably sodium hydride; the temperature at which compound 5 is added dropwise may be −10~50° C., preferably 0~20° C.; the rate at which compound 5 is added dropwise may be from 1 g/min to 100 g/min, preferably 10 g/min; the organic base used may be selected from the group consisting of lithium diisopropylethylamide, n-butyllithium, tert-butyllithium, sodium ethoxide, sodium ethoxide, sodium tert-butoxide, and a mixture thereof in any ratio, preferably n-butyllithium; the acidic aqueous solution for quenching may be selected from the group consisting of hydrochloric acid, sodium bisulfate, ammonium chloride, sodium hydrogen phosphate, and a mixture thereof in any ratio, preferably a diluted solution of hydrochloric acid having a mass percentage concentration of 3%; and the organic solvent for extraction may be selected from the group consisting of toluene, 2-methyltetrahydrofuran, dichloromethane, methyl tert-butyl ether, and a mixture thereof in any ratio, preferably methyl tert-butyl ether.

The specific process of step 4) may comprise the followings. Tert-pentyl 6-(benzyloxy)-3,5-dioxo-hexanoate (compound 6) is evenly dispersed in a solvent. After stirring to homogeneity, a reductase, formic acid or a formate salt and NAD$^+$ are added. pH is adjusted to 6.2~6.4 with an aqueous solution of formic acid or the like. The system is warmed up to 27~33° C., and the temperature is maintained for 17~24 h. After the reaction is completed, the system is warmed up to 65~70° C. to destroy the enzyme protein. An organic solvent is added, and the system is filtered with a diatomaceous earth pad. The liquid is separated, and the aqueous phase is reversely extracted with an organic solvent. The organic phase is combined and concentrated. The resultant product can be used directly in the next step. The purity of the product obtained in step 4) is 92~95%, the yield is 70~85%, the ee value is above 99.5%, and the de value is 90~99.5%.

In the above step 4): the solvent for dispersing compound 6 may be selected from the group consisting of purified water, polyethylene glycol, isopropanol, acetonitrile, tetrahydrofuran, ethanol, n-heptane, toluene, acetone, DMF and methanol, preferably purified water; the volume of the solvent for dispersing may be 1~10 times, preferably 4 times, relative to the volume of compound 6; the amount of the reductase may be 0.05~4 mg/g, preferably 0.1 mg/g, relative to the amount of compound 6; the overall reaction volume may be 10~60 times, preferably 30 times, relative to the volume of compound 6; the molar ratio of formic acid or a formate salt to compound 6 may be from 2:1 to 10:1, preferably 2:1; the formate salt may be selected from the group consisting of ammonium formate, sodium formate, potassium formate, preferably ammonium formate; the mass ratio of $NAD^+$ to compound 6 may be from 0.001:1 to 0.1:1, preferably 0.03:1; the range of pH may be 4.0~9.0, preferably 6.2+0.2; and the organic solvent used for extraction may be selected from the group consisting of ethyl acetate, isopropyl acetate, tetrahydrofuran, dichloromethane, diethyl ether, methyl tert-butyl ether, n-heptane, toluene, xylene, and a mixture thereof in any ratio, preferably isopropyl acetate.

The specific process of step 5) may comprise the followings. Tert-pentyl (3R,5S)-6-benzyloxy-3,5-dihydroxyhexanoate (compound 7), 2,2-dimethoxypropane and catalytic amount of an acid are added sequentially to an organic solvent. The reaction is continued until compound 7 is substantially consumed. An acid was added for washing, followed by adding an alkali for neutralizing the system. The low boiling-point substances are removed under reduced pressure, followed by adding water, separating the liquid, and extracting the aqueous phase several times with an organic solvent. The organic phase is combined and washed once with saturated brine. The organic phase is filtered with a silica gel pad, and the filtrate is concentrated. The resultant product is directly used in the next step. The purity of the product obtained in step 5) is 92~95%, and the yield is 88~92%.

In the above step 5): the organic solvent for reaction may be selected from the group consisting of methanol, acetone, acetonitrile, dichloromethane, toluene, tetrahydrofuran, methyl tert-butyl ether, and a mixture thereof in any ratio, preferably acetone; the volume of the organic solvent may be 3~20 times, preferably 10 times, relative to the volume of compound 7; the reaction temperature may be −10~60° C., preferably 15~25° C.; the molar ratio of the added 2,2-dimethoxypropane to compound 7 may be from 1:1 to 10:1, preferably 2:1; the added acid in a catalytic amount may be selected from the group consisting of hydrochloric acid, sulfuric acid, pyridinium p-toluene sulfonate, p-methylbenzene sulfonic acid, acetic acid, and a mixture thereof in any ratio, preferably pyridinium p-toluene sulfonate; the mass ratio of the added acid in a catalytic amount to compound 7 may be from 0.01:1 to 0.1:1, preferably 0.02:1; the acid added for washing may be selected from the group consisting of hydrochloric acid, sulfuric acid, p-methylbenzene sulfonic acid, acetic acid, and a mixture thereof in any ratio, preferably diluted hydrochloric acid having a mass percentage concentration of 3%; the mass ratio of the acid added for washing to compound 7 may be from 0.01:1 to 1:1, preferably 0.05:1; the alkali added for neutralizing the system may be selected from the group consisting of sodium hydroxide, potassium hydroxide, sodium bicarbonate, potassium bicarbonate, potassium carbonate, and a mixture thereof in any ratio, preferably saturated aqueous solution of sodium bicarbonate; and the solvent for extracting in the post-treatment may be selected from the group consisting of ethyl acetate, diethyl ether, methyl tert-butyl ether, n-heptane, toluene, xylene, and a mixture thereof in any ratio, preferably ethyl acetate.

The specific process of step 6) may comprise the followings. Tert-pentyl (4R-cis)-6-(benzyloxy)-2,2-dimethyl-1,3-dioxane-4-hexnoate (compound 8) and a metallic catalyst is added to an organic solvent. The system is sealed and displaced with nitrogen five times and with hydrogen three times. The reaction is continued until compound 8 is substantially consumed. The pressure is released and the autoclave is opened. The mixture is taken out and suctioned. The cake is washed twice with an organic solvent. The product obtained by concentrating is directly used in the next oxidation reaction. The purity of the product is 95-98%, and the yield is 92-95%.

In the above step 6): the organic solvent for reaction may be selected from the group consisting of methanol, acetone, ethanol, acetonitrile, ethyl acetate, dichloromethane, tetrahydrofuran, methyl tert-butyl ether, and a mixture thereof in any ratio, preferably ethyl acetate; the volume of the reaction solvent, ethyl acetate, may be 3~20 times, preferably 10 times, relative to the volume of compound 8; the added metallic catalyst may be selected from the group consisting of palladium hydroxide, palladium on carbon, platinum on carbon, platinum oxide, Raney-Ni, and a mixture thereof in any ratio, preferably palladium hydroxide; the mass ratio of the added metallic catalyst to compound 8 may be from 0.01:1 to 1:1, preferably 0.05:1; and the solvent for washing the cake may be selected from the group consisting of methanol, acetone, ethanol, acetonitrile, ethyl acetate, dichloromethane, tetrahydrofuran, methyl tert-butyl ether, and a mixture thereof in any ratio, preferably ethyl acetate.

The specific process of step 7) may comprise the followings. 2-((4R,6S)-6-methoxy-2,2-dimethyl-[1,3]dioxan-4-yl)-acetate (compound 9) is added to an organic solvent. The mixture is cooled down, followed by adding dimethyl sulfoxide and a certain amount of an alkali. An oxidant is added in portions. After compound 9 is reacted completely, water is added to quench the reaction. The liquid is separated and the aqueous phase is reversely extracted with an organic solvent. The organic phase is combined, washed with purified water, and concentrated to give the target compound (compound of formula I). The purity of the target product is 92-96%, and the yield is 80-85%.

In the above step 7): the organic solvent for reaction may be selected from the group consisting of acetone, acetonitrile, ethyl acetate, dichloromethane, tetrahydrofuran, methyl tert-butyl ether, toluene, N,N-dimethylformamide, N,N-dimethylacetamide, and a mixture thereof in any ratio, preferably dichloromethane; the volume of the organic solvent for reaction may be 3~20 times, preferably 10 times, relative to the volume of compound 9; the molar ratio of the added dimethyl sulfoxide to compound 9 may be from 0.01:1 to 20:1, preferably 10:1; the added alkali may be selected from the group consisting of triethylamine, pyridine, ethylene diamine, N,N-diisopropylethylamine, and a mixture thereof in any ratio, preferably N,N-diisopropylethylamine; the molar ratio of the added alkali to compound 9 may be from 1:1 to 50:1, preferably 3.5:1; the added oxidant may be selected from the group consisting of sodium hypochlorite-TEMPO, sulfur trioxide pyridine-dimethyl sulfoxide, active manganese dioxide, PCC oxidant, PDC oxidant, DMP, preferably sulfur trioxide pyridine; the molar ratio of the added oxidant to compound 9 may be from 0.01:1 to 20:1, preferably 10:1; the rate at which the oxidant is added may be from 0.01 Kg/h to 1 Kg/h, preferably 0.4 Kg/h; the volume of water used for quenching the reaction may be 3~20 times, preferably 5 times, relative to the volume of compound 9; and the solvent for extraction in the post-treatment may be selected from the group consisting of ethyl acetate, dichloromethane, methyl tert-butyl ether, toluene, n-heptane, and a mixture thereof in any ratio, preferably dichloromethane.

The specific process for preparing the acetylacetate of formula (5) may comprise the following. An alcohol (compound 10), a reaction solvent and a catalyst are added to a reaction flask. While controlling the temperature of the system, diketen is added dropwise. The temperature is maintained and the reaction is continued until the starting materials are completely reacted. The reaction solvent and excessive diketen are removed by distillation, and the acetylacetate (compound 5) is obtained by rectification under reduced pressure.

In the above process: the catalyst used may be selected from the group consisting of sodium acetate, piperidine, isopropylamine, 4-dimethylaminopyridine, and other compound capable of catalyzing this kind of reaction; the molar ratio of the catalyst to the alcohol (compound 10) may be 0.01~0.5:1, preferably 0.05~0.10:1; the reaction solvent used may be tetrahydrofuran, toluene or acetonitrile, or the reaction may be conducted without a solvent; the reaction temperature may be −10~110° C., preferably 10~70° C.; the molar ratio of the diketen to the alcohol may be 0.5~3:1, preferably 1~1.2:1; and the resultant compound may be purified by distillation under reduced pressure, or other chemical purification processes known in the art.

The reductase used in the above preparation method may be any existing diketoreductase or a mutant thereof. In a preferred embodiment of the preparation method of the present invention, the reductase is a diketoreductase mutant comprising one of the amino acid sequences shown below:
a) SEQ ID NO: 1 to SEQ ID NO: 6;
b) a sequence having at least 70% identity to a sequence shown in a) and having improved diketoreductase activities; or
c) a sequence obtained by deleting, adding and/or replacing one or more amino acid residues in a sequence shown in a) and having improved diketoreductase activities,
wherein the sequence shown in b) is not a sequence shown in SEQ ID NO: 7.

The above diketoreductase mutant may be obtained by a process comprising gene mutation and directional screening, using diketoreductase (DKR) gene (shown in SEQ ID NO: 7) of *Rhodococcus erythropolis* SK121 strain as the starting gene. The amino acid sequence contains the following sequences:
(1) the amino acid sequence shown in SEQ ID NO: 1, with the mutation site at F231W:

MTELKQITVLGTGVLGSQIAYQTACHGFDVVAYDINAEVIEKAKARFDSL

AAAYKAENVEGAKEGKADEALQRITYSYDLGEAVAKADLVIEAIPEDIAI

KRDTYEKLATVAPEHTVFATNSSTLLPSDLKEFTGRPEKFLALHFANHVW

VNNTAEVMGTESTDPAVYREVVEFAKNIGMVPIELKKEKAGYVLNSLLVP

LLNAASDLLIDGIADPDMVDKTWRIGTGAPWGPFQIMDVVGLTTVYNISS

QGGEKQREFADYIKKNYIDEGKLGVAVGDGFYNYKG;

(2) the amino acid sequence shown in SEQ ID NO: 2, with the mutation sites at I94V+F231W:

MTELKQITVLGTGVLGSQIAYQTACHGFDVVAYDINAEVIEKAKARFDSL

AAAYKAENVEGAKEGKADEALQRITYSYDLGEAVAKADLVIEAVPEDIAI

KRDTYEKLATVAPEHTVFATNSSTLLPSDLKEFTGRPEKFLALHFANHVW

VNNTAEVMGTESTDPAVYREVVEFAKNIGMVPIELKKEKAGYVLNSLLVP

LLNAASDLLIDGIADPDMVDKTWRIGTGAPWGPFQIMDVVGLTTVYNISS

QGGEKQREFADYIKKNYIDEGKLGVAVGDGFYNYKG;

(3) the amino acid sequence shown in SEQ ID NO: 3, with the mutation sites at I94V+V151Q+F231 W:

MTELKQITVLGTGVLGSQIAYQTACHGFDVVAYDINAEVIEKAKARFDSL

AAAYKAENVEGAKEGKADEALQRITYSYDLGEAVAKADLVIEAVPEDIAI

KRDTYEKLATVAPEHTVFATNSSTLLPSDLKEFTGRPEKFLALHFANHVW

QNNTAEVMGTESTDPAVYREVVEFAKNIGMVPIELKKEKAGYVLNSLLVP

LLNAASDLLIDGIADPDMVDKTWRIGTGAPWGPFQIMDVVGLTTVYNISS

QGGEKQREFADYIKKNYIDEGKLGVAVGDGFYNYKG;

(4) the amino acid sequence shown in SEQ ID NO: 4, with the mutation sites at V239I+R257K:

MTELKQITVLGTGVLGSQIAYQTACHGFDVVAYDINAEVIEKAKARFDSL

AAAYKAENVEGAKEGKADEALQRITYSYDLGEAVAKADLVIEAIPEDIAI

KRDTYEKLATVAPEHTVFATNSSTLLPSDLKEFTGRPEKFLALHFANHVW

VNNTAEVMGTESTDPAVYREVVEFAKNIGMVPIELKKEKAGYVLNSLLVP

LLNAASDLLIDGIADPDMVDKTWRIGTGAPFGPFQIMDIVGLTTVYNISS

QGGEKQKEFADYIKKNYIDEGKLGVAVGDGFYNYKG;

(5) the amino acid sequence shown in SEQ ID NO: 5, with the mutation sites at V151Q+R257K

MTELKQITVLGTGVLGSQIAYQTACHGFDVVAYDINAEVIEKAKARFDSL

AAAYKAENVEGAKEGKADEALQRITYSYDLGEAVAKADLVIEAIPEDIAI

KRDTVEKLATVAPEHTVFATNSSTLLPSDLKEFTGRPEKFLALHFANHVW

QNNTAEVMGTESTDPAVYREVVEFAKNIGMVPIELKKEKAGYVLNSLLVP

LLNAASDLLIDGIADPDMVDKTWRIGTGAPFGPFQIMDVVGLTTVYNISS

QGGEKQKEFADYIKKNYIDEGKLGVAVGDGFYNYKG;
or (6) the amino acid sequence shown in SEQ ID NO: 6, with the mutation sites at I94V+V151Q:

MTELKQITVLGTGVLGSQIAYQTACHGFDVVAYDINAEVIEKAKARFDSL

AAAYKAENVEGAKEGKADEALQRITYSYDLGEAVAKADLVIEAVPEDIAI

KRDTYEKLATVAPEHTVFATNSSTLLPSDLKEFTGRPEKFLALHFANHVW

QNNTAEVMGTESTDPAVYREVVEFAKNIGMVPIELKKEKAGYVLNSLLVP

LLNAASDLLIDGIADPDMVDKTWRIGTGAPFGPFQIMDVVGLTTVYNISS

QGGEKQREFADYIKKNYIDEGKLGVAVGDGFYNYKG.

The encoding DNA sequences of the above diketoreductase mutants include the following DNA sequences:
(1) SEQ ID NO: 9, corresponding to the diketoreductase gene sequence shown in SEQ ID NO: 8 wherein TC at 691-693 bp is mutated to TGG;
(2) SEQ ID NO: 10, corresponding to the diketoreductase gene sequence shown in SEQ ID NO: 8 wherein TTC at 691-693 bp is mutated to TGG, and ATT at 280-282 bp is mutated to GTT, GTC, GTA or GTG;
(3) SEQ ID NO: 11, corresponding to the diketoreductase gene sequence shown in SEQ ID NO: 8 wherein TC at 691-693 bp is mutated to TGG, ATT at 280-282 bp is mutated to GIT, GTC, GTA or GTG, and GTC at 451-453 bp is mutated to CAA or CAG;
(4) SEQ ID NO: 12, corresponding to the diketoreductase gene sequence shown in SEQ ID NO: 8 wherein GTC at 715-717 bp is mutated to ATT, ATC or ATA, and CGC at 769-771 bp is mutated to AAA or AAG;
(5) SEQ ID NO: 13, corresponding to the diketoreductase gene sequence shown in SEQ ID NO: 8 wherein GTC at 451-453 bp is mutated to CAA or CAG, and CGC at 769-771 bp is mutated to AAA or AAG; or
(6) SEQ ID NO: 14, corresponding to the diketoreductase gene sequence shown in SEQ ID NO: 8 wherein GTC at 451-453 bp is mutated to CAA or CAG, and ATT at 280-282 bp is mutated to GTr, GTC, GTA or GTG.

The term "identity" used in the present invention has the meaning generally known in the field, and the rules and standards for determining the identity of different sequences are well known for a person skilled in the art. The sequences defined with different levels of identity in the present invention should also have improved diketoreductase activities. The methods and means for determining the activity of a diketoreductase and for screening mutant sequences are well known for a person skilled in the art. Such mutant sequences would be readily obtainable for a person skilled in the art under the teachings of the disclosure in the present application. In some embodiments, the sequence of the diketoreductase mutant has at least about 75%, 80%, 85%, 90%, 91%, 92%, 93%, 94%, 95%, 96%, 97%, 98%, 99%, 99.1%, 99.2%, 99.3%, 99.4%, 99.5%, 99.6% identity to the sequence shown in SEQ ID No: 7 or 8 and has or encodes an amino acid sequence having an improved diketoreductase activity. For example, one or more amino acid residues, such as one or several amino acid residues, such as 1, 2, 3, 4, 5, 6, 8, 9, 10, 15, 20, 30, 40, 50 amino acid residues, in said amino acid sequence can undergo conservative amino acid substitution. The conservative amino acids are well known in the art.

The term "improved diketoreductase activity" used herein means that the diketoreductase obtained using the technology of site-directed saturation mutagenesis has improved bioactivity in comparison with the initial diketoreductase, such as improved catalytic activity, broader substrate profile, increased thermal stability, increased pH stability or increased expression, for example increasing by at least 5%, 10%, 20%, 30%, 40%, 50%, 100%, 150%, 200%, 500% or more in comparison with the initial diketoreductase.

In order to sufficiently illustrate the present invention, the preparation method of the present application is verified in the following examples. The examples are provided for exemplary explanation and as specific representatives, and should not be construed or understood as limitations to the scope of the present application.

All the experimental materials in the examples are commercially available unless otherwise indicated. Although the description in the examples of the present application starts from the starting compound, a person skilled in the art would understand that the process of the examples of the present application can start from any intermediate and step in case a certain intermediate product is available.

EXAMPLE 1: Preparation and Screening of Diketoreductase Mutant

1. Site-Directed Saturation Mutagenesis of Diketoreductase (DKR) (SEQ ID NO: 7) Derived from *Rhodococcus erythropolis* SK121 Strain The three-dimensional protein structure of the amino acid sequence of diketoreductase (DKR) was simulated on the website of Swiss-model, and the binding between the substrate and the protein was simulated by Docking, and the amino acids which may be correlated to the binding between the substrate and NAD and to NAD proton transfer were finally selected as mutant amino acids through Pymol analysis.

Based on mutant amino acids and the base sequences on both sides thereof (for the mutant amino acids, see the mutation sites in Table 1), corresponding mutant primers were designed with Primmer5.0 (Table 1). Using pET22b(+) expression vector comprising diketoreductase gene (purchased from Novagen, catalog No. 69744) as the template, complete linear segments were obtained through whole plasmid PCR. The above PCR product, after being digested with DPnI to remove the parent template, was transformed into *Escherichia coli* BL21 (DE3), coated in LB culture dishes comprising 50 μg/ml of ampicillin, and cultured overnight at 37° C.

TABLE 1

Sequences of primers for site-directed saturation mutagenesis

| SEQ ID NO. | Mutation Sites | Names of Primer | Primer Sequences |
|---|---|---|---|
| 15 | I94 | I94-Forward | GGTCATCGAGGCANNNCCCGAGGACATCG |
| 16 |  | I94-Reverse | CGATGTCCTCGGGNNNTGCCTCGATGACC |
| 17 | E96 | E96-Forward | GTCATCGAGGCAATTCCCNNNGACATCGCCATCAAGCG |

TABLE 1-continued

Sequences of primers for site-directed saturation mutagenesis

| SEQ ID NO. | Mutation Sites | Names of Primer | Primer Sequences |
|---|---|---|---|
| 18 | | E96-Reverse | CGCTTGATGGCGATGTCNNNGGGAATTGCCTCGATGAC |
| 19 | R102 | R102-Forward | GAGGACATCGCCATCAAGNNNGACACCTACGAGAAGCTTG |
| 20 | | R102-Reverse | CAAGCTTCTCGTAGGTGTCNNNCTTGATGGCGATGTCCTC |
| 21 | T124 | T124-Forward | CTACCAACTCCTCGNNNCTGCTGCCGAGCG |
| 22 | | T124-Reverse | CGCTCGGCAGCAGNNNCGAGGAGTTGGTAG |
| 23 | S123 | S123-Forward | CGCTACCAACTCCNNNACGCTGCTGCCGAG |
| 24 | | S123-Reverse | CTCGGCAGCAGCGTNNNGGAGTTGGTAGCG |
| 25 | H148 | H148-Forward | CACTTCGCAAATNNNGTGTGGGTCAAC |
| 26 | | H148-Reverse | GTTGACCCACACNNNATTTGCGAAGTGG |
| 27 | V151Q | V151-Forward | CAAATCACGTGTGGNNNAACAACACTGCC |
| 28 | | V151-Reverse | GGCAGTGTTGTTNNNCCACACGTGATTTG |
| 29 | E156 | E156-Forward | CAACAACACTGCCNNNGTCATGGGCACCG |
| 30 | | E156-Reverse | CGGTGCCCATGACNNNGGCAGTGTTGTTG |
| 31 | K189 | K189-Forward | GAACTCAAGAAGGAGNNNGCGGGCTACGTACTC |
| 32 | | K189-Reverse | GAGTACGTAGCCCGCNNNCTCCTTCTTGAGTTC |
| 33 | G191 | G191-Forward | GAACTCAAGAAGGAGAAGGCGNNNTACGTACTCAACTCGC |
| 34 | | G191-Reverse | GCGAGTTGAGTACGTANNNCGCCTTCTCCTTCTTGAGTTC |
| 35 | L194 | L194-Forward | CGGGCTACGTANNNAACTCGCTCCTGG |
| 36 | | L194-Reverse | CCAGGAGCGAGTTNNNTACGTAGCCCG |
| 37 | W223 | W223-Forward | GGTCGACAAGACGNNNCGTATCGGCACCGG |
| 38 | | W223-Reverse | CCGGTGCCGATACGNNNCGTCTTGTCGACC |
| 39 | F231 | F231-Forward | TATCGGCACCGGAGCCCCGNNNGGCCCCTTCCAGATCATG |
| 40 | | F231-Reverse | CATGATCTGGAAGGGGCCNNNCGGGGCTCCGGTGCCGATA |
| 41 | M237 | M237-Forward | GCCCCTTCCAGATCNNNGACGTCGTCGGGTTG |
| 42 | | M237-Reverse | CAACCCGACGACGTCNNNGATCTGGAAGGGGC |
| 43 | V239 | V239-Forward | CTTCCAGATCATGGACNNNGTCGGGTTGACCAC |
| 44 | | V239-Reverse | GTGGTCAACCCGACNNNGTCCATGATCTGGAAG |
| 45 | V240 | V240-Forward | GATCATGGACGTCNNNGGGTTGACCAC |
| 46 | | V240-Reverse | GTGGTCAACCCNNNGACGTCCATGATC |
| 47 | N247 | N247-Forward | GACCACCGTCTACNNNATCTCCTCCCAGG |
| 48 | | N247-Reverse | CCTGGGAGGAGATNNNGTAGACGGTGGTC |
| 49 | Q251 | Q251-Forward | CAACATCTCCTCCNNNGGCGGCGAGAAGC |
| 50 | | Q251-Reverse | GCTTCTCGCCGCCNNNGGAGGAGATGTTG |
| 51 | R257 | R257-Forward | CCCAGGGCGGCGAGAAGCAGNNNGAATTCGCCGACTACATCAAG |
| 52 | | R257-Reverse | CTTGATGTAGTCGGCGAATTCNNNCTGCTTCTCGCCGCCCTGGG |
| 53 | L273 | L273-Forward | CATCGACGAGGGCAAGNNNGGCGTTGCTGTC |
| 54 | | L273-Reverse | GACAGCAACGCCNNNCTTGCCCTCGTCGATG |
| 55 | A276 | A276-Forward | CGAGGGCAAGCTCGGCGTTNNNGTCGGCGACGGCTTCTAC |
| 56 | | A276-Reverse | GTAGAAGCCGTCGCCGACNNNAACGCCGAGCTTGCCCTCG |

2. Preliminary Screening of Diketoreductase Mutants

Single colonies on the culture dishes described above in step 1 were selected and inoculated into a deep-well 96-well plate, each well being pre-added with 0.5 ml of LB liquid culture medium comprising 50 μg/ml of ampicillin. After oscillating and culturing at 37° C. for 3 h, IPTG was added with a final concentration of 0.2 mM, and the expression was induced at 18° C. for 16 h. The thalli were collected by centrifuging at 6000 g for 10 min, and the cells were broken with a sonicator (JY92-2D, Ningbo Scientz Biotechnology Co., Ltd). A supernatant was obtained by centrifuging at 10000 g for 20 min at 4° C., and was subjected to preliminary screening for its activity with a microplate reader. 30 μL of DMSO, 1.5 μL of the main starting material, tert-butyl 6-benzyloxy-3,5-dioxo-hexanoate (30 mg/mL in DMSO), 2.5 μL of NADH (20 mg/mL), and 216 μL of phosphate buffer (100 mM, pH=6.0) were added into the 96-well plate, and the background was detected at 340 nm. To each well was then added 50 μL of mutant enzyme liquid which was prepared in advance, and the change in the absorbance was immediately detected at 340 nm and at 30° C.

The equation for calculating enzyme activity is as follows:

$$\text{Enzyme activity (u/mL)} = (\Delta A \times 60 \times V_1)/(6.22 \times t \times V_2)$$

wherein:

ΔA: change in the absorbance during the reaction;

$V_1$: total volume of the reaction system;

6.22: extinction coefficient;

t: time at which ΔA is detected;

$V_1$: volume of the added enzyme liquid.

3. Secondary Screening of Diketoreductase Mutants

The mutants in step 2 having higher enzyme activities than the parent enzyme were inoculated into 500 ml of LB liquid culture medium comprising 50 μg/ml of ampicillin. After oscillating and culturing at 37° C. until $OD_{600}$=0.6, IPTG was added with a final concentration of 0.2 mM, and the expression was induced at 18° C. After 16 h, the thalli were collected by centrifuging at 6000 g for 10 min. The thalli were broken with a sonicator (JY92-2D, Ningbo Scientz Biotechnology Co., Ltd). A supernatant was obtained by centrifuging at 10000 g for 20 min at 4° C., which was used for activity detection. 0.05 g of the main starting material,

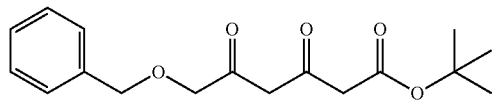 [SMILES: CC(C)(C)OC(=O)CC(=O)CC(=O)COCc1ccccc1]

(tert-butyl 6-benzyloxy-3,5-dioxo-hexanoate), and 0.5 ml of polyethylene glycol PEG-400 were added into a 10 ml reaction flask. After the starting materials were dissolved, 4.0 ml of phosphate buffer (100 mM, pH=6.0) was added, and the main starting material was evenly dispersed in the buffer; 1.5 mg of $NAD^+$, 20.6 mg of ammonium formate, 10 mg of co-enzyme formate dehydrogenase and 0.5 ml of diketoreductase were added, and the system had pH=6.0. After maintaining the temperature at 30±3° C. for 16 h, the samples were monitored with thin layer chromatography (TLC). The systems with distinct transformation point and vague point of the main starting material were selected and extracted with ethyl acetate. After standing still, the liquid was separated, and the organic phase was taken for HPLC analysis.

The mutants having higher catalytic activities than the parent enzyme were selected for sequencing to analyze the mutation sites, and for scale-up culture. By re-testing the catalytic activities, it was determined that the mutants F231W (SEQ ID NO: 1), I94V+F231W (SEQ ID NO: 2), I94V+V151Q+F231W (SEQ ID NO: 3), V239I+R257K (SEQ ID NO: 4), V151Q+R257K (SEQ ID NO: 5) and I94V+V151Q (SEQ ID NO: 6) had significantly higher catalytic activities than the parent enzyme. The results of the secondary screening were shown in Table 2. By simulating and analyzing the three-dimensional structure of the diketoreductase with a computer software, it was determined that I94 was located in the NAD-binding region, and four amino acids V151, F231, V239 and R257 were all near the substrate-binding site. The changes in these amino acids may increase the specificity of substrate binding, so that the enzyme activity was improved.

TABLE 2

Comparison of the activities of parent diketoreductase and mutants in the preparation of tert-butyl 3R,5S-dihydroxy-6-benzyloxy-hexanoate

| SEQ ID NO | Site | Amount of Enzyme[a] | Conversion | DE % | EE % |
|---|---|---|---|---|---|
| 1 | F231W | 3 wt | 82.70 | 87.66 | 100.00 |
| 2 | I94V + F231W | 2 wt | 72.91 | 89.89 | 100.00 |
| 3 | I94V + V151Q + F231W | 2 wt | 78.31 | 89.44 | 100.00 |
| 4 | V239I + R257K | 2 wt | 68.26 | 85.24 | 100.00 |
| 5 | V151Q + R257K | 2 wt | 62.27 | 88.69 | 100.00 |
| 6 | I94V + V151Q | 3 wt | 68.46 | 88.14 | 100.00 |
| 7 | Parent strain | 6 wt | 62.26 | 87.45 | 100.00 |

Note:
[a]wet weight of each diketoreductase mutant recombined cells needed for converting 1 g substrate; 1 wt means that 1 g diketoreductase mutant recombined wet cells was need for 1 g main starting material.

4. Cloning and Expressing of Diketoreductase Mutants

In order to facilitate the expression and identification of the diketoreductase mutants, compatible restrictive enzyme digestion sites were designed at 5' and 3' ends of the gene. Nde I and Xho I may be used for enzyme digestion of the target gene and pET-22b(+) (other expression plasmids which can express proteins in Escherichia coli can also be used) respectively and simultaneously. The relatively large fragments of the target gene and plasmid after enzyme digestion were ligated with T4 DNA ligase. The ligated product was transformed into competent cells of Escherichia coli DH5α strains. The transformed competent cells were then coated onto a LB culture plate comprising 50 μg/ml of ampicillin, and cultured overnight at 37° C.

Single colonies grown on the above culture dishes were selected and inoculated into a LB liquid culture medium comprising 50 μg/ml of ampicillin. After oscillating and culturing overnight at 37° C., the thalli were collected for plasmid collection. After PCR identification and identification of double enzyme digestion, the correct cloning vectors were named pET22b(+)-R-M and were transformed into Escherichia coli BL21(DE3). The transformed Escherichia coli BL21(DE3) were coated onto a LB culture plate comprising 50 μg/ml of ampicillin, and cultured overnight at 37° C. Single colonies grown on the above culture plate were selected and inoculated into 5 ml LB liquid culture medium comprising 50 μg/ml of ampicillin, and identified with colony PCR. The Escherichia coli comprising correct expression vectors were subjected to subsequent induced expression. The above bacteria liquid was transferred to 500 ml of LB liquid culture medium comprising 50 μg/ml of ampicillin. After oscillating and culturing at 37° C. until $OD_{600}$=0.5~0.6, IPTG was added with a final concentration of 0.2~1.0 mM, and the expression was induced at 18~25° C. for 10~16 h. The bacteria liquid was taken out. The thalli were collected by centrifuging at 6000 g for 10 min, and stored at −20° C. for further use. The thalli were broken with a sonicator (JY92-2D, Ningbo Scientz Biotechnology Co., Ltd). A supernatant and a precipitate were obtained by centrifuging at 10000 g for 20 min at 4° C. The supernatant was subjected to SDS-PAGE test with a vertical electrophoresis system. The expressed diketoreductase mutant was shown to have a molecular weight of about 30 KD in SDS-PAGE.

EXAMPLE 2: Preparation of the Chiral Intermediate for Use in Statin Drugs (1) Synthesis of Benzyloxyacetic Acid (Compound 3)

960 g of tetrahydrofuran and 41 g of toluene were added into a reaction flask. While controlling the temperature of the system at 10-20° C., 534.0 g of potassium hydroxide was added in four portions. After the addition of potassium hydroxide was completed, 1371.1 g of benzyl alcohol was added into the system in three portions. 300.1 g of chloroacetic acid was dissolved in 480.5 g of tetrahydrofuran, and the solution of chloroacetic acid in tetrahydrofuran was added dropwise into the above system while maintaining the temperature at 70-80° C. The system was reacted until chloroacetic acid was completely consumed. After cooling the system down, 3.12 Kg of purified water was added and tetrahydrofuran was removed under reduced pressure. The aqueous phase was extracted four times with toluene, and adjusted with hydrochloric acid at 10-20° C. to pH 3. The aqueous phase was extracted twice with methyl tert-butyl ether, and then concentrated to give 421.3 g of benzyloxyacetic acid (compound 3). The yield was 88.3%, and the GC purity was ≥99.2%.

$^1$H NMR (400 MHz, CDCl$_3$) δ: 12.28 (br, 1H), 7.34-7.30 (m, 5H), 4.59 (s, 2H), 4.12 (s, 2H).

(2) Synthesis of 2-benzyloxy-morpholine Acetamide (Compound 4)

700.5 g of dichloromethane and 110.1 g of compound 3 were added into a reaction flask. While controlling the temperature of the system at 10-20° C., 575.3 g of oxalyl chloride was added dropwise. After the addition of oxalyl chloride was completed, the system was stirred for 1 h and concentrated to remove low boiling-point substances. The concentrated liquid is stored for further use. 48.0 g of morpholine, 75.5 g of triethylamine and 480.1 of g toluene were added into a reaction flask. While controlling the temperature at about 10° C., the above concentrated liquid was added dropwise into the reaction system. After the addition was completed, the system was stirred for 1 h. Diluted hydrochloric acid was then added to quench the reaction. The liquid was separated. The organic phase was washed sequentially with water, saturated sodium bicarbonate and water, and concentrated to give 116.0 g of 2-benzyloxy-morpholine acetamide (compound 4). The yield was 90.3%, and the HPLC purity was ≥97.5%.

$^1$H NMR (400 MHz, CDCl$_3$) δ: 7.33-7.28 (m, 5H), 4.56 (s, 2H), 4.14 (s, 2H), 3.63-3.57 (m, 6H), 3.45-3.44 (br, 2H).

(3) Synthesis of tert-pentyl acetylacetate (Compound 5a)

500 g of tert-pentyl alcohol and 34.6 g of 4-dimethylaminopyridine were dissolved in 2.5 L of anhydrous tetrahydrofuran. After cooling down to about 5° C., 524.3 g of freshly distilled diketen was added slowly and dropwise. After the addition was completed, the temperature was returned to about 20° C. for reaction until the reaction was completed as confirmed by TLC monitoring. The solvent and excessive diketen were removed by distillation, and the material was purified by distillation under reduced pressure (5~8 mmHg, 80~90° C.) to give 732.5 g of tert-pentyl acetylacetate (compound 5a). The yield was 75.2%, and the GC purity was ≥98.5%.

$^1$H NMR (CDCl$_3$, 400 MHz) δ 6.11 (s, 2H), 3.39 (s, 2H), 2.28 (s, 3H), 1.81 (q, J=7.4 Hz, 2H), 1.47 (s, 6H), 0.92 (t, J=7.5 Hz, 3H).

(4) Synthesis of Cyclopentyl 6-(benzyloxy)-3,5-dioxo-hexanoate (Compound 6a)

72.3 g of sodium hydride was dispersed in 1600.1 g of tetrahydrofuran. While controlling the temperature at about 10° C., 387.3 g of tert-pentyl acetylacetate was added dropwise. After cooling down to about –20° C., 722.5 mL of n-butyllithium was added slowly and dropwise. After the addition was completed, 300.3 g of compound 4 was further added dropwise. After the reaction was completed as confirmed by TLC monitoring, diluted hydrochloric acid was added into the system to quench the reaction. After separating the liquid, the aqueous phase was extracted with methyl tert-butyl ether. The organic phase was combined and concentrated to give 200.8 g of cyclopentyl 6-(benzyloxy)-3,5-dioxo-hexanoate (compound 6a). The yield was 70.0%, and the HPLC purity was ≥98.2%.

$^1$H NMR (400 MHz, CDCl$_3$) δ: 7.32-7.23 (m, 5H), 6.08 (s, 2H), 5.23 (s, 2H), 3.24 (s, 2H), 3.09 (s, 2H), 1.14-1.02 (m, 8H), 0.88 (t, J=7.6 Hz, 3H).

(5) Synthesis of tert-pentyl (3R,5S)-6-(benzyloxy)-3,5-dihydroxyhexanoate (Compound 7a)

Purified water (4.0 mL/g compound 6a) and tert-pentyl 6-(benzyloxy)-3,5-dioxo-hexanoate (compound 6a, 1.0 mol) were added into a reaction flask. After stirring to homogeneity, crude enzyme liquid of diketoreductase mutant I94V+F231W, ammonium formate (2.0 mol) and NAD$^+$ (0.03 mol) were added, wherein the mass of the reductase mutant was 0.1 mg/g relative to the mass of compound 6a. After adjusting pH=6.2~6.4, the system was warmed up to about 30° C., and the temperature was maintained for about 20 h. After the reaction was completed, the system was warmed up to 65~70° C. to destroy the enzyme protein. Ethyl acetate was added, and the mixture was passed through a silica gel pad. After separating the liquid, the aqueous phase was reversely extracted with ethyl acetate. The organic phase was combined and concentrated to give the product tert-pentyl (3R, 5S)-6-(benzyloxy)-3,5-dihydroxyhexanoate (compound 7a). The purity was 95%, the yield was 73.1%, the ee value was above 99.3%, and the de value was 93.5%.

$^1$H NMR (400 MHz, CDCl$_3$): δ: 7.37-7.30 (m, 5H), 6.12 (s, 2H), 4.59 (d, J=7.2 Hz, 2H), 4.31 (br, 1H), 4.14 (br, 1H), 3.09 (s, 2H), 1.14-1.02 (m, 8H), 0.88 (t, J=7.6 Hz, 3H).

(6) Synthesis of tert-pentyl (4R-cis)-6-(benzyloxy)-2,2-dimethyl-1,3-dioxane-4-hexanoate (Compound 8a)

Acetone (10.0 mL/g compound 7a), tert-pentyl (3R,5S)-6-benzyloxy-3,5-dihydroxyhexanoate (compound 7a, 1.0 mol), 2,2-dimethoxypropane (2.0 mol) and catalytic amount of pyridinium p-toluene sulfonate (0.02 mol) were added into a reaction flask, and stirred. The system was reacted at about 20° C. until the starting material (compound 7a) was substantially consumed. Diluted hydrochloric acid having a mass percentage concentration of 3% (0.05 mol) was added for washing, followed by adding saturated aqueous solution of sodium bicarbonate to neutralize the system. Low boiling-point substances were removed under reduced pressure, followed by adding water. After separating the liquid, the aqueous phase was extracted twice with ethyl acetate. The organic phase was combined and washed once with saturated brine. The organic phase was passed through a silica gel pad and concentrated to give the product tert-pentyl (4R-cis)-6-(benzyloxy)-2,2-dimethyl-1,3-dioxane-4-hexanoate (compound 8a). The purity was 93.5%, and the yield was 90.3%.

$^1$H NMR (400 MHz, CDCl$_3$) δ: 7.35-7.28 (m, 5H), 6.13 (s, 2H), 4.80 (d, J=7.5 Hz, 2H), 4.33-4.28 (m, 1H), 4.12-4.07 (m, 1H), 2.87-2.64 (m, 2H), 1.83-1.79 (m, 2H), 1.37-1.29 (m, 14H), 0.88 (t, J=7.5 Hz, 3H).

(7) Synthesis of tert-pentyl (4R-cis)-6-hydroxymethyl-2,2-dimethyl-1,3-dioxane-4-hexanoate (Compound 9a)

Ethyl acetate (10.0 mL/g compound 8a), tert-pentyl (4R-cis)-6-(benzyloxy)-2,2-dimethyl-1,3-dioxane-4-hexanoate (compound 8a, 1.0 mol) and a metallic catalyst palladium hydroxide (5%) were added into a reaction flask, and stirred. The system was sealed, followed by displacing with nitrogen five times and with hydrogen three times. The system was reacted at about 20° C. until the starting material (compound 8a) was substantially consumed. The system was displaced with nitrogen three times, and the pressure was released. The system was suctioned and the cake was washed twice with ethyl acetate. The filtrate and the washing liquid were combined and concentrated to dryness to give the product tert-pentyl (4R-cis)-6-hydroxymethyl-2,2-dimethyl-1,3-dioxane-4-hexanoate (compound 9a). The purity of the product was 96.7%, and the yield was 93.9%.

$^1$H NMR (400 MHz, CDCl$_3$) δ: 4.33-4.26 (m, 1H), 4.01-3.98 (m, 1H), 3.81-3.48 (m, 2H), 2.46-2.30 (m, 2H), 1.79-1.76 (m, 2H), 1.42-1.33 (m, 14H), 0.88 (t, J=7.6 Hz, 3H).

(8) Synthesis of tert-pentyl (4R-cis)-6-formyl-2,2-dimethyl-1,3-dioxane-4-hexanoate (Compound Ia)

Dichloromethane (10.0 mL/g compound 9a) and 2-((4R,6S)-6-methoxy-2,2-dimethyl-[1,3]dioxan-4-yl)-acetate (compound 9a, 1.0 mol) were added into a reaction flask, and stirred. The system was cooled down to −10~0° C., followed by adding dimethyl sulfoxide (10.0 mol) and N,N-diisopropylethylamine (3.5 mol), and adding sulfur trioxide pyridine (3.25 mol) in portions. After the addition was completed, the mixture was reacted while maintaining the temperature until compound 9a was substantially consumed. Purified water was then added to the system to quench the reaction. The liquid was separated and the aqueous phase was reversely extracted once with dichloromethane. The organic phase was combined, washed with purified water, and concentrated to dryness to give the target side chain product tert-pentyl (4R-cis)-6-formyl-2,2-dimethyl-1,3-dioxane-4-hexanoate (formula Ia). The purity of the product was 93.2%, and the yield was 82.5%.

$^1$H NMR (400 MHz, CDCl$_3$) δ: 9.58 (s, 1H), 4.34-4.30 (m, 2H), 2.43-2.37 (m, 2H), 2.46-2.30 (m, 2H), 1.57-1.43 (m, 2H), 1.43-1.36 (m, 12H), 0.89 (t, J=7.8 Hz, 3H).

EXAMPLE 3: Preparation of the Chiral Intermediate for Use in Statin Drugs (1) Synthesis of Benzyloxyacetic Acid (Compound 3)

720.3 g of tetrahydrofuran and 41.1 g of toluene were added into a reaction flask. While controlling the temperature of the system at 10-20° C., 382.1 g of sodium hydroxide was added in four portions. After the addition of sodium hydroxide was completed, 1371.1 g of benzyl alcohol was added into the system in three portions. 300.2 g of chloroacetic acid was dissolved in 720.5 g of tetrahydrofuran, and the solution of chloroacetic acid in tetrahydrofuran was added dropwise into the above system while maintaining the temperature at 70-80° C. The system was reacted until chloroacetic acid was completely consumed. After cooling the system down, 3.1 Kg of purified water was added and tetrahydrofuran was removed under reduced pressure. The aqueous phase was extracted four times with toluene, and adjusted with hydrochloric acid at 10-20° C. to pH 3.2. The aqueous phase was extracted twice with methyl tert-butyl ether, and then concentrated to give 410.5 g of benzyloxyacetic acid (compound 3). The yield was 86.2%, and the GC purity was ≥99.1%.

$^1$H NMR (400 MHz, CDCl$_3$) δ: 12.28 (br, 1H), 7.34-7.30 (m, 5H), 4.59 (s, 2H), 4.12 (s, 2H).

(2) Synthesis of 2-benzyloxy-morpholine Acetamide (Compound 4)

700.0 g of toluene and 110.1 g of compound 3 were added into a reaction flask. While controlling the temperature of the system at 10-20° C., 557.3 g of thionyl chloride was added dropwise. After the addition of thionyl chloride was completed, the system was stirred for 1 h and concentrated to remove low boiling-point substances. The concentrated liquid is stored for further use. 48.0 g of morpholine, 75.1 g of triethylamine and 480.0 g of toluene were added into a reaction flask. While controlling the temperature at about 15° C., the above concentrated liquid was added dropwise into the reaction system. After the addition was completed, the system was stirred for 1 h. Diluted hydrochloric acid was then added to quench the reaction. The liquid was separated. The organic phase was washed sequentially with water, saturated sodium bicarbonate and water, and concentrated to give 116.3 g of 2-benzyloxy-morpholine acetamide (compound 4). The yield was 90.2%, and the HPLC purity was ≥97.5%.

1H NMR (400 MHz, CDCl3) δ: 7.33-7.28 (m, 5H), 4.56 (s, 2H), 4.14 (s, 2H), 3.63-3.57 (m, 6H), 3.45-3.44 (br, 2H).

(3) Synthesis of tert-pentyl acetylacetate (Compound 5a)

500.0 g of tert-pentyl alcohol and 34.6 g of 4-dimethylaminopyridine were dissolved in 2.5 L of anhydrous tetrahydrofuran. After cooling down to about 5° C., 524.2 g of freshly distilled diketen was added slowly and dropwise. After the addition was completed, the temperature was returned to about 15° C. for reaction until the reaction was completed as confirmed by TLC monitoring. The solvent and excessive diketen were removed by distillation, and the material was purified by distillation under reduced pressure (5~8 mmHg, 80~90° C.) to give 732.2 g of tert-pentyl acetylacetate (compound 5a). The yield was 75.3%, and the GC purity was ≥98.5%.

$^1$H NMR (CDCl$_3$, 400 MHz) δ 6.11 (s, 2H), 3.39 (s, 2H), 2.28 (s, 3H), 1.81 (q, J=7.4 Hz, 2H), 1.47 (s, 6H), 0.92 (t, J=7.5 Hz, 3H).

(4) Synthesis of Cyclopentyl 6-(benzyloxy)-3,5-dioxohexanoate (Compound 6a)

144.6 g of sodium hydroxide was dispersed in 1600.2 g of tetrahydrofuran. While controlling the temperature at about 10° C., 387.5 g of tert-pentyl acetylacetate was added dropwise. After cooling down to about −20° C., 722 mL of diisopropylethyllithium was added slowly and dropwise. After the addition was completed, 300.2 g of compound 4 was further added dropwise. After the reaction was completed as confirmed by TLC monitoring, diluted hydrochloric acid was added into the system to quench the reaction. After separating the liquid, the aqueous phase was extracted with methyl tert-butyl ether. The organic phase was combined and concentrated to give 194.8 g of cyclopentyl 6-(benzyloxy)-3,5-dioxo-hexanoate (compound 6a). The yield was 68.2%, and the HPLC purity was ≥98.3%.

$^1$H NMR (400 MHz, CDCl$_3$) δ: 7.32-7.23 (m, 5H), 6.08 (s, 2H), 5.23 (s, 2H), 3.24 (s, 2H), 3.09 (s, 2H), 1.14-1.02 (m, 8H), 0.88 (t, J=7.6 Hz, 3H).

(5) Synthesis of tert-pentyl (3R,5S)-6-(benzyloxy)-3,5-dihydroxyhexanoate (Compound 7a)

Purified water (4.0 mL/g compound 6a) and tert-pentyl 6-(benzyloxy)-3,5-dioxo-hexanoate (compound 6a, 1.0 mol) were added into a reaction flask. After stirring to homogeneity, crude enzyme liquid of diketoreductase mutant I94V+V151Q+F231W, ammonium formate (2.0 mol) and NAD$^+$ (0.03 mol) were added, wherein the mass of the mutant was 0.1 mg/g relative to the mass of compound 6a. After adjusting pH=6.2~6.4, the system was warmed up to about 30° C., and the temperature was maintained for about 20 h. After the reaction was completed, the system was warmed up to 65~70° C. to destroy the enzyme protein. Ethyl acetate was added, and the mixture was passed through a silica gel pad. After separating the liquid, the aqueous phase was reversely extracted with ethyl acetate. The organic phase, was combined and concentrated to give the product tert-pentyl (3R, 5S)-6-(benzyloxy)-3,5-dihydroxyhexanoate (compound 7a). The purity was 93.1%, the yield was 73.2%, the ee value was above 99.3%, and the de value was 92.8%.

$^1$H NMR (400 MHz, CDCl$_3$) δ: 7.37-7.30 (m, 5H), 6.12 (s, 2H), 4.59 (d, J=7.2 Hz, 2H), 4.31 (br, 1H), 4.14 (br, 1H), 3.09 (s, 2H), 1.14-1.02 (m, 8H), 0.88 (t, J=7.6 Hz, 3H).

(6) Synthesis of tert-pentyl (4R-cis)-6-(benzyloxy)-2,2-dimethyl-1,3-dioxane-4-hexanoate (Compound 8a)

Acetone (10.0 mL/g compound 7a), tert-pentyl (3R,5S)-6-benzyloxy-3,5-dihydroxyhexanoate (compound 7a, 1.0 mol), 2,2-dimethoxypropane (2.0 mol) and catalytic amount of hydrochloric acid (0.02 mol) were added into a reaction flask, and stirred. The system was reacted at about 25° C. until the starting material compound 7a was substantially consumed. Diluted hydrochloric acid having a mass percentage concentration of 3% (0.05 mol) was added for washing, followed by adding saturated aqueous solution of sodium bicarbonate to neutralize the system. Low boiling-point substances were removed under reduced pressure, followed by adding water. After separating the liquid, the aqueous phase was extracted twice with ethyl acetate. The organic phase was combined and washed once with saturated brine. The organic phase was passed through a silica gel pad and concentrated to give the product tert-pentyl (4R-cis)-6-(benzyloxy)-2,2-dimethyl-1,3-dioxane-4-hexanoate (compound 8a). The purity was 94.0%, and the yield was 90.2%.

$^1$H NMR (400 MHz, CDCl$_3$) δ: 7.35-7.28 (m, 5H), 6.13 (s, 2H), 4.80 (d, J=7.5 Hz, 2H), 4.33-4.28 (m, 1H), 4.12-4.07 (m, 1H), 2.87-2.64 (m, 2H), 1.83-1.79 (m, 2H), 1.37-1.29 (m, 14H), 0.88 (t, J=7.5 Hz, 3H).

(7) Synthesis of tert-pentyl (4R-cis)-6-hydroxymethyl-2,2-dimethyl-1,3-dioxane-4-hexanoate (Compound 9a)

Ethyl acetate (10.0 mL/g compound 8a), tert-pentyl (4R-cis)-6-(benzyloxy)-2,2-dimethyl-1,3-dioxane-4-hexanoate (compound 8a, 1.0 mol) and a metallic catalyst palladium hydroxide (5%) were added into a reaction flask, and stirred. The system was sealed, followed by displacing with nitrogen five times and with hydrogen three times. The system was reacted at about 25° C. until the starting material compound 8a was substantially consumed. The system was displaced with nitrogen three times, and the pressure was released. The system was suctioned and the cake was washed twice with ethyl acetate. The filtrate and the washing liquid were combined and concentrated to dryness to give the product tert-pentyl (4R-cis)-6-hydroxymethyl-2,2-dimethyl-1,3-dioxane-4-hexanoate (compound 9a). The purity of the product was 96.3%, and the yield was 92.6%.

$^1$H NMR (400 MHz, CDCl$_3$) δ: 4.33-4.26 (m, 1H), 4.01-3.98 (m, 1H), 3.81-3.48 (m, 2H), 2.46-2.30 (m, 2H), 1.79-1.76 (m, 2H), 1.42-1.33 (m, 14H), 0.88 (t, J=7.6 Hz, 3H).

(8) Synthesis of tert-pentyl (4R-cis)-6-formyl-2,2-dimethyl-1,3-dioxane-4-hexanoate (Compound Ia)

Dichloromethane (10.0 mL/g compound 9a) and 2-((4R,6S)-6-methoxy-2,2-dimethyl-[1,3]dioxan-4-yl)-acetate (compound 9a, 1.0 mol) were added into a reaction flask, and stirred. The system was cooled down to −10~0° C., followed by adding dimethyl sulfoxide (10 mol) and triethylamine (3.5 mol), and adding sulfur trioxide pyridine (3.25 mol) in portions. After the addition was completed, the mixture was reacted while maintaining the temperature until compound 9a was substantially consumed. Purified water was then added to the system to quench the reaction. The liquid was separated and the aqueous phase was reversely extracted once with dichloromethane. The organic phase was combined, washed with purified water, and concentrated to dryness to give the target side chain product tert-pentyl (4R-cis)-6-formyl-2,2-dimethyl-1,3-dioxane-4-hexanoate (formula Ia). The purity of the product was 95.1%, and the yield was 82.7%.

$^1$H NMR (400 MHz, CDCl$_3$) δ: 9.58 (s, 1H), 4.34-4.30 (m, 2H), 2.43-2.37 (m, 2H), 2.46-2.30 (m, 2H), 1.57-1.43 (m, 2H), 1.43-1.36 (m, 12H), 0.89 (t, J=7.8 Hz, 3H).

EXAMPLE 4: Preparation of the Chiral Intermediate for Use in Statin Drugs

The preparation process was similar to that in Example 1, except that the acetylacetate is cyclopentyl acetylacetate. The preparation process comprises the following steps:

500.0 g of cyclopentyl alcohol and 20.5 g of isopropylamine were cooled down to about 5° C., followed by adding 500.0 g of freshly distilled diketen slowly and dropwise. After the addition was completed, the system was warmed up to 60~70° C. for reaction until the reaction was completed as confirmed by TLC monitoring. The system is cooled down to below 40° C., followed by removing excessive diketen by distillation to give 790.5 g of cyclopentyl acetylacetate (compound 5b). The yield was 80.2%, and the GC purity was ≥97.5%.

$^1$H NMR (CDCl$_3$, 400 MHz) δ 5.22 (t, J=5.8 Hz, 1H), 3.40 (s, 2H), 2.25 (s, 3H), 1.91-1.79 (m, 2H), 1.78-1.66 (m, 5H), 1.65-1.53 (m, 2H).

Although preferable embodiments of the present application are disclosed in order to illustrate the present application, a person skilled in art should understand that various modifications, additions and replacements can be made to the present application without departing from the concept and scope of the present application as defined by the Claims.

The invention claimed is:
1. A method for preparing a chiral intermediate of formula (I) for use in statin drugs, characterized in that the method comprises the following steps:
   1) conducting an etherification reaction by contacting chloroacetic acid (1) and benzyl alcohol (2) as starting materials to produce benzyloxy acetic acid (3);
   2) conducting a condensation reaction by contacting benzyloxy acetic acid (3) and morpholine to produce 2-benzyloxymorpholine acetamide (4);
   3) conducting a substitution reaction by contacting 2-benzyloxymorpholine acetamide (4) and an acetylacetate ester of formula (5) to produce a diketone intermediate of formula (6);
   4) conducting an asymmetric reduction reaction of the diketone intermediate of formula (6) to produce a chiral diol intermediate of formula (7) by contacting said diketone intermediate of formula (6) with a reductase, wherein the reductase is a diketoreductase mutant comprising an amino acid sequence selected from the group consisting of SEQ ID NO: 1, 2, 3, 4, 5, and 6:
   5) reacting the chiral diol intermediate of formula (7) with 2,2-dimethoxypropane to produce (4R-cis)-6-(benzyloxy)-2,2-dimethyl-1,3-dioxane-4-hexanoate ester of formula (8);
   6) removing the benzyl group from the (4R-cis)-6-(benzyloxy)-2,2-dimethyl-1,3-dioxane-4-hexanoate ester of formula (8) to produce (4R-cis)-6-hydroxymethyl-2,2-dimethyl-1,3-dioxane-4-hexanoate ester of formula (9); and
   7) conducting oxidation reaction of the (4R-cis)-6-hydroxymethyl-2,2-dimethyl- 1,3-dioxane-4-hexanoate ester of formula (9) to give the chiral intermediate of formula (I),
wherein the method is as follows:

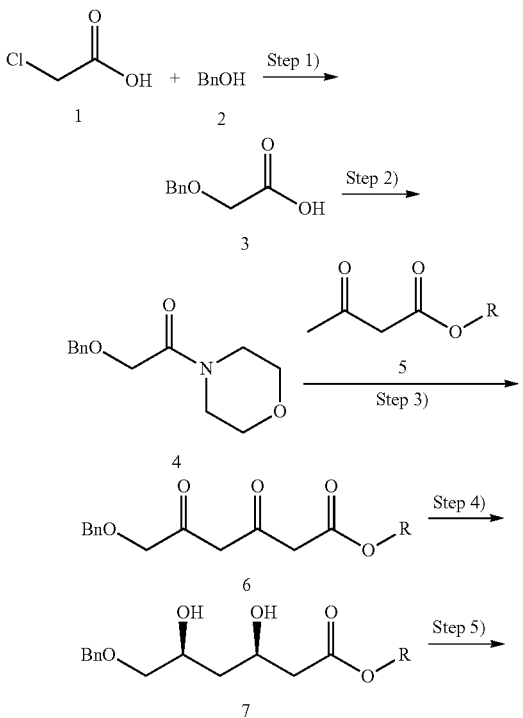

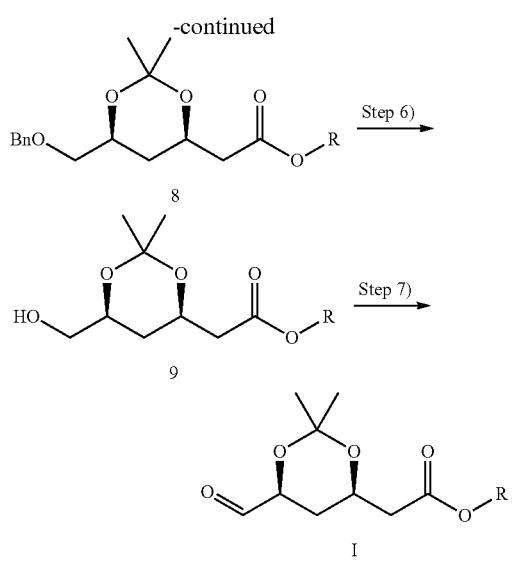

wherein R represents C4-C10 alkyl.

2. The method of claim 1, wherein R represents tert-butyl, tert-pentyl, cyclopentyl or cyclohexyl.

3. The method of claim 1, wherein the acetylacetate ester of formula (5) is prepared through a ring opening addition reaction between diketene and an alcohol of formula (10); wherein the reaction is as follows:

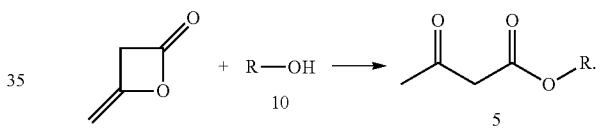

4. The method of claim 1, wherein the asymmetric reduction reaction in step 4) comprises: evenly dispersing the diketone intermediate of formula (6) in a solvent, adding the reductase, formic acid or a formate salt and NAD+, adjusting the pH value to 6.2-6.4, then warming the asymmetric reduction reaction up to 27°-33° C., and maintaining the temperature for 17-24 h.

5. The method of claim 4, wherein the mass ratio of the reductase to the diketone intermediate of formula (6) is 0.00005-0.004:1.

6. The method of claim 4, wherein the solvent is one or more selected from the group consisting of purified water, polyethylene glycol, isopropanol, acetonitrile, tetrahydrofuran, ethanol, n-heptane, toluene, acetone, dimethylformamide and methanol.

7. The method of claim 4, wherein the formate salt is selected from the group consisting of ammonium formate, sodium formate and potassium formate, and the molar ratio of formic acid or formate salt to the diketone intermediate of formula (6) is 2-10:1.

8. The method of claim 4, wherein the mass ratio of NAD+ to the diketone intermediate of formula (6) is 0.001-0.1:1.

* * * * *

SEQUENCE LISTING

```
<160> NUMBER OF SEQ ID NOS: 56

<210> SEQ ID NO 1
<211> LENGTH: 286
<212> TYPE: PRT
<213> ORGANISM: Artificial Sequence
<220> FEATURE:
<223> OTHER INFORMATION: Diketoreductase Mutant

<400> SEQUENCE: 1
```

```
Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30

Tyr Asp Ile Asn Ala Glu Val Ile Glu Lys Ala Lys Ala Arg Phe Asp
        35                  40                  45

Ser Leu Ala Ala Ala Tyr Lys Ala Glu Asn Val Glu Gly Ala Lys Glu
50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Ile Pro Glu
                85                  90                  95

Asp Ile Ala Ile Lys Arg Asp Thr Tyr Glu Lys Leu Ala Thr Val Ala
            100                 105                 110

Pro Glu His Thr Val Phe Ala Thr Asn Ser Ser Thr Leu Leu Pro Ser
        115                 120                 125

Asp Leu Lys Glu Phe Thr Gly Arg Pro Glu Lys Phe Leu Ala Leu His
    130                 135                 140

Phe Ala Asn His Val Trp Val Asn Asn Thr Ala Glu Val Met Gly Thr
145                 150                 155                 160

Glu Ser Thr Asp Pro Ala Val Tyr Arg Glu Val Val Glu Phe Ala Lys
                165                 170                 175

Asn Ile Gly Met Val Pro Ile Glu Leu Lys Lys Glu Lys Ala Gly Tyr
            180                 185                 190

Val Leu Asn Ser Leu Leu Val Pro Leu Leu Asn Ala Ala Ser Asp Leu
        195                 200                 205

Leu Ile Asp Gly Ile Ala Asp Pro Asp Met Val Asp Lys Thr Trp Arg
    210                 215                 220

Ile Gly Thr Gly Ala Pro Trp Gly Pro Phe Gln Ile Met Asp Val Val
225                 230                 235                 240

Gly Leu Thr Thr Val Tyr Asn Ile Ser Ser Gln Gly Gly Glu Lys Gln
                245                 250                 255

Arg Glu Phe Ala Asp Tyr Ile Lys Lys Asn Tyr Ile Asp Glu Gly Lys
            260                 265                 270

Leu Gly Val Ala Val Gly Asp Gly Phe Tyr Asn Tyr Lys Gly
        275                 280                 285

<210> SEQ ID NO 2
<211> LENGTH: 286
<212> TYPE: PRT
<213> ORGANISM: Artificial Sequence
<220> FEATURE:
<223> OTHER INFORMATION: Diketoreductase Mutant

<400> SEQUENCE: 2

Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30

Tyr Asp Ile Asn Ala Glu Val Ile Glu Lys Ala Lys Ala Arg Phe Asp
        35                  40                  45

Ser Leu Ala Ala Ala Tyr Lys Ala Glu Asn Val Glu Gly Ala Lys Glu
50                  55                  60

Gly Lys Ala Asp Glu Ala Leu Gln Arg Ile Thr Tyr Ser Tyr Asp Leu
65                  70                  75                  80
```

```
Gly Glu Ala Val Ala Lys Ala Asp Leu Val Ile Glu Ala Val Pro Glu
                85                  90                  95

Asp Ile Ala Ile Lys Arg Asp Thr Tyr Glu Lys Leu Ala Thr Val Ala
            100                 105                 110

Pro Glu His Thr Val Phe Ala Thr Asn Ser Ser Thr Leu Leu Pro Ser
        115                 120                 125

Asp Leu Lys Glu Phe Thr Gly Arg Pro Glu Lys Phe Leu Ala Leu His
    130                 135                 140

Phe Ala Asn His Val Trp Val Asn Asn Thr Ala Glu Val Met Gly Thr
145                 150                 155                 160

Glu Ser Thr Asp Pro Ala Val Tyr Arg Glu Val Val Glu Phe Ala Lys
                165                 170                 175

Asn Ile Gly Met Val Pro Ile Glu Leu Lys Lys Glu Lys Ala Gly Tyr
            180                 185                 190

Val Leu Asn Ser Leu Leu Val Pro Leu Leu Asn Ala Ala Ser Asp Leu
        195                 200                 205

Leu Ile Asp Gly Ile Ala Asp Pro Asp Met Val Asp Lys Thr Trp Arg
    210                 215                 220

Ile Gly Thr Gly Ala Pro Trp Gly Pro Phe Gln Ile Met Asp Val Val
225                 230                 235                 240

Gly Leu Thr Thr Val Tyr Asn Ile Ser Ser Gln Gly Gly Glu Lys Gln
                245                 250                 255

Arg Glu Phe Ala Asp Tyr Ile Lys Lys Asn Tyr Ile Asp Glu Gly Lys
            260                 265                 270

Leu Gly Val Ala Val Gly Asp Gly Phe Tyr Asn Tyr Lys Gly
        275                 280                 285

<210> SEQ ID NO 3
<211> LENGTH: 286
<212> TYPE: PRT
<213> ORGANISM: Artificial Sequence
<220> FEATURE:
<223> OTHER INFORMATION: Diketoreductase Mutant

<400> SEQUENCE: 3

Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30

Tyr Asp Ile Asn Ala Glu Val Ile Glu Lys Ala Lys Ala Arg Phe Asp
        35                  40                  45

Ser Leu Ala Ala Ala Tyr Lys Ala Glu Asn Val Glu Gly Ala Lys Glu
    50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Val Pro Glu
                85                  90                  95

Asp Ile Ala Ile Lys Arg Asp Thr Tyr Glu Lys Leu Ala Thr Val Ala
            100                 105                 110

Pro Glu His Thr Val Phe Ala Thr Asn Ser Ser Thr Leu Leu Pro Ser
        115                 120                 125

Asp Leu Lys Glu Phe Thr Gly Arg Pro Glu Lys Phe Leu Ala Leu His
    130                 135                 140

Phe Ala Asn His Val Trp Gln Asn Asn Thr Ala Glu Val Met Gly Thr
145                 150                 155                 160
```

-continued

Glu Ser Thr Asp Pro Ala Val Tyr Arg Glu Val Val Glu Phe Ala Lys
            165                 170                 175

Asn Ile Gly Met Val Pro Ile Glu Leu Lys Lys Glu Lys Ala Gly Tyr
            180                 185                 190

Val Leu Asn Ser Leu Leu Val Pro Leu Leu Asn Ala Ala Ser Asp Leu
            195                 200                 205

Leu Ile Asp Gly Ile Ala Asp Pro Asp Met Val Asp Lys Thr Trp Arg
            210                 215                 220

Ile Gly Thr Gly Ala Pro Trp Gly Pro Phe Gln Ile Met Asp Val Val
225                 230                 235                 240

Gly Leu Thr Thr Val Tyr Asn Ile Ser Ser Gln Gly Gly Glu Lys Gln
            245                 250                 255

Arg Glu Phe Ala Asp Tyr Ile Lys Lys Asn Tyr Ile Asp Glu Gly Lys
            260                 265                 270

Leu Gly Val Ala Val Gly Asp Gly Phe Tyr Asn Tyr Lys Gly
            275                 280                 285

<210> SEQ ID NO 4
<211> LENGTH: 286
<212> TYPE: PRT
<213> ORGANISM: Artificial Sequence
<220> FEATURE:
<223> OTHER INFORMATION: Diketoreductase Mutant

<400> SEQUENCE: 4

Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30

Tyr Asp Ile Asn Ala Glu Val Ile Glu Lys Ala Lys Ala Arg Phe Asp
            35                  40                  45

Ser Leu Ala Ala Ala Tyr Lys Ala Glu Asn Val Glu Gly Ala Lys Glu
            50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Ile Pro Glu
            85                  90                  95

Asp Ile Ala Ile Lys Arg Asp Thr Tyr Glu Lys Leu Ala Thr Val Ala
            100                 105                 110

Pro Glu His Thr Val Phe Ala Thr Asn Ser Ser Thr Leu Leu Pro Ser
            115                 120                 125

Asp Leu Lys Glu Phe Thr Gly Arg Pro Glu Lys Phe Leu Ala Leu His
            130                 135                 140

Phe Ala Asn His Val Trp Val Asn Asn Thr Ala Glu Val Met Gly Thr
145                 150                 155                 160

Glu Ser Thr Asp Pro Ala Val Tyr Arg Glu Val Val Glu Phe Ala Lys
            165                 170                 175

Asn Ile Gly Met Val Pro Ile Glu Leu Lys Lys Glu Lys Ala Gly Tyr
            180                 185                 190

Val Leu Asn Ser Leu Leu Val Pro Leu Leu Asn Ala Ala Ser Asp Leu
            195                 200                 205

Leu Ile Asp Gly Ile Ala Asp Pro Asp Met Val Asp Lys Thr Trp Arg
            210                 215                 220

Ile Gly Thr Gly Ala Pro Phe Gly Pro Phe Gln Ile Met Asp Ile Val
225                 230                 235                 240

-continued

```
Gly Leu Thr Thr Val Tyr Asn Ile Ser Ser Gln Gly Gly Glu Lys Gln
                245                 250                 255

Lys Glu Phe Ala Asp Tyr Ile Lys Lys Asn Tyr Ile Asp Glu Gly Lys
            260                 265                 270

Leu Gly Val Ala Val Gly Asp Gly Phe Tyr Asn Tyr Lys Gly
        275                 280                 285

<210> SEQ ID NO 5
<211> LENGTH: 286
<212> TYPE: PRT
<213> ORGANISM: Artificial Sequence
<220> FEATURE:
<223> OTHER INFORMATION: Diketoreductase Mutant

<400> SEQUENCE: 5

Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Ala
                20                  25                  30

Tyr Asp Ile Asn Ala Glu Val Ile Glu Lys Ala Lys Ala Arg Phe Asp
            35                  40                  45

Ser Leu Ala Ala Ala Tyr Lys Ala Glu Asn Val Glu Gly Ala Lys Glu
        50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Ile Pro Glu
                85                  90                  95

Asp Ile Ala Ile Lys Arg Asp Thr Tyr Glu Lys Leu Ala Thr Val Ala
            100                 105                 110

Pro Glu His Thr Val Phe Ala Thr Asn Ser Ser Thr Leu Leu Pro Ser
        115                 120                 125

Asp Leu Lys Glu Phe Thr Gly Arg Pro Glu Lys Phe Leu Ala Leu His
130                 135                 140

Phe Ala Asn His Val Trp Gln Asn Asn Thr Ala Glu Val Met Gly Thr
145                 150                 155                 160

Glu Ser Thr Asp Pro Ala Val Tyr Arg Glu Val Val Glu Phe Ala Lys
                165                 170                 175

Asn Ile Gly Met Val Pro Ile Glu Leu Lys Lys Glu Lys Ala Gly Tyr
            180                 185                 190

Val Leu Asn Ser Leu Leu Val Pro Leu Leu Asn Ala Ala Ser Asp Leu
        195                 200                 205

Leu Ile Asp Gly Ile Ala Pro Asp Met Val Asp Lys Thr Trp Arg
210                 215                 220

Ile Gly Thr Gly Ala Pro Phe Gly Pro Phe Gln Ile Met Asp Val Val
225                 230                 235                 240

Gly Leu Thr Thr Val Tyr Asn Ile Ser Ser Gln Gly Gly Glu Lys Gln
                245                 250                 255

Lys Glu Phe Ala Asp Tyr Ile Lys Lys Asn Tyr Ile Asp Glu Gly Lys
            260                 265                 270

Leu Gly Val Ala Val Gly Asp Gly Phe Tyr Asn Tyr Lys Gly
        275                 280                 285

<210> SEQ ID NO 6
<211> LENGTH: 286
<212> TYPE: PRT
<213> ORGANISM: Artificial Sequence
<220> FEATURE:
```

<223> OTHER INFORMATION: Diketoreductase Mutant

<400> SEQUENCE: 6

Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30

Tyr Asp Ile Asn Ala Glu Val Ile Glu Lys Ala Lys Ala Arg Phe Asp
        35                  40                  45

Ser Leu Ala Ala Ala Tyr Lys Ala Glu Asn Val Glu Gly Ala Lys Glu
    50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Val Pro Glu
                85                  90                  95

Asp Ile Ala Ile Lys Arg Asp Thr Tyr Glu Lys Leu Ala Thr Val Ala
            100                 105                 110

Pro Glu His Thr Val Phe Ala Thr Asn Ser Ser Thr Leu Leu Pro Ser
        115                 120                 125

Asp Leu Lys Glu Phe Thr Gly Arg Pro Glu Lys Phe Leu Ala Leu His
    130                 135                 140

Phe Ala Asn His Val Trp Gln Asn Asn Thr Ala Glu Val Met Gly Thr
145                 150                 155                 160

Glu Ser Thr Asp Pro Ala Val Tyr Arg Glu Val Val Glu Phe Ala Lys
                165                 170                 175

Asn Ile Gly Met Val Pro Ile Glu Leu Lys Lys Glu Lys Ala Gly Tyr
            180                 185                 190

Val Leu Asn Ser Leu Leu Val Pro Leu Leu Asn Ala Ala Ser Asp Leu
        195                 200                 205

Leu Ile Asp Gly Ile Ala Asp Pro Asp Met Val Asp Lys Thr Trp Arg
    210                 215                 220

Ile Gly Thr Gly Ala Pro Phe Gly Pro Phe Gln Ile Met Asp Val Val
225                 230                 235                 240

Gly Leu Thr Thr Val Tyr Asn Ile Ser Ser Gln Gly Gly Glu Lys Gln
                245                 250                 255

Arg Glu Phe Ala Asp Tyr Ile Lys Lys Asn Tyr Ile Asp Glu Gly Lys
            260                 265                 270

Leu Gly Val Ala Val Gly Asp Gly Phe Tyr Asn Tyr Lys Gly
        275                 280                 285

<210> SEQ ID NO 7
<211> LENGTH: 286
<212> TYPE: PRT
<213> ORGANISM: Rhodococcus erythropolis

<400> SEQUENCE: 7

Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30

Tyr Asp Ile Asn Ala Glu Val Ile Glu Lys Ala Lys Ala Arg Phe Asp
        35                  40                  45

Ser Leu Ala Ala Ala Tyr Lys Ala Glu Asn Val Glu Gly Ala Lys Glu
    50                  55                  60

Gly Lys Ala Asp Glu Ala Leu Gln Arg Ile Thr Tyr Ser Tyr Asp Leu

```
         65                  70                  75                  80
Gly Glu Ala Val Ala Lys Ala Asp Leu Val Ile Glu Ala Ile Pro Glu
                 85                  90                  95
Asp Ile Ala Ile Lys Arg Asp Thr Tyr Glu Lys Leu Ala Thr Val Ala
                100                 105                 110
Pro Glu His Thr Val Phe Ala Thr Asn Ser Ser Thr Leu Leu Pro Ser
                115                 120                 125
Asp Leu Lys Glu Phe Thr Gly Arg Pro Glu Lys Phe Leu Ala Leu His
            130                 135                 140
Phe Ala Asn His Val Trp Val Asn Asn Thr Ala Glu Val Met Gly Thr
145                 150                 155                 160
Glu Ser Thr Asp Pro Ala Val Tyr Arg Glu Val Glu Phe Ala Lys
                165                 170                 175
Asn Ile Gly Met Val Pro Ile Glu Leu Lys Lys Glu Lys Ala Gly Tyr
                180                 185                 190
Val Leu Asn Ser Leu Leu Val Pro Leu Leu Asn Ala Ala Ser Asp Leu
                195                 200                 205
Leu Ile Asp Gly Ile Ala Asp Pro Asp Met Val Asp Lys Thr Trp Arg
            210                 215                 220
Ile Gly Thr Gly Ala Pro Phe Gly Pro Phe Gln Ile Met Asp Val Val
225                 230                 235                 240
Gly Leu Thr Thr Val Tyr Asn Ile Ser Ser Gln Gly Gly Glu Lys Gln
                245                 250                 255
Arg Glu Phe Ala Asp Tyr Ile Lys Lys Asn Tyr Ile Asp Glu Gly Lys
                260                 265                 270
Leu Gly Val Ala Val Gly Asp Gly Phe Tyr Asn Tyr Lys Gly
            275                 280                 285

<210> SEQ ID NO 8
<211> LENGTH: 861
<212> TYPE: DNA
<213> ORGANISM: Rhodococcus erythropolis

<400> SEQUENCE: 8
atgactgaac tgaagcagat caccgttctg ggtaccggag ttctcggctc acagatcgcc      60
tatcagaccg cctgtcacgg tttcgacgtc gtcgcgtacg acatcaacgc cgaggtcatc     120
gaaaaggcca aggctcggtt cgactcgttg ccgcggcct acaaggccga aacgtcgag      180
ggtgccaagg aaggcaaggc tgacgaagcg ctgcaacgta ttacgtactc gtacgatcta     240
ggcgaagccc tcgccaaggc cgacctggtc atcgaggcaa ttcccgagga catcgccatc     300
aagcgcgaca cctacgagaa gcttgccacg gttgctcctg agcacacggt gttcgctacc     360
aactcctcga cgctgctgcc gagcgatctc aaggagttca ccggccgtcc cgagaagttc     420
ctcgcactgc acttcgcaaa tcacgtgtgg gtcaacaaca ctgccgaggt catgggcacc     480
gagtccaccg accccgccgt gtaccgcgag gtcgtcgagt tcgcgaagaa catcggcatg     540
gtgccgatcg aactcaagaa ggagaaggcg ggctacgtac tcaactcgct cctggtcccg     600
ctcctcaacg cggcctccga cctgctgatc gacggcatcg ccgatcccga catggtcgac     660
aagacgtggc gtatcggcac cggagccccg ttcggcccct tccagatcat ggacgtcgtc     720
gggttgacca ccgtctacaa catctcctcc cagggcggcg agaagcagcg cgaattcgcc     780
gactacatca agaagaacta catcgacgag ggcaagctcg gcgttgctgt cggcgacggc     840
ttctacaact acaagggctg a                                              861
```

<210> SEQ ID NO 9
<211> LENGTH: 861
<212> TYPE: DNA
<213> ORGANISM: Artificial Sequence
<220> FEATURE:
<223> OTHER INFORMATION: Diketoreductase Mutant Coded Sequence

<400> SEQUENCE: 9

| | |
|---|---|
| atgactgaac tgaagcagat caccgttctg ggtaccggag ttctcggctc acagatcgcc | 60 |
| tatcagaccg cctgtcacgg tttcgacgtc gtcgcgtacg acatcaacgc cgaggtcatc | 120 |
| gaaaaggcca aggctcggtt cgactcgttg gccgcggcct acaaggccga aacgtcgag | 180 |
| ggtgccaagg aaggcaaggc tgacgaagcg ctgcaacgta ttacgtactc gtacgatcta | 240 |
| ggcgaagccg tcgccaaggc cgacctggtc atcgaggcaa ttcccgagga catcgccatc | 300 |
| aagcgcgaca cctacgagaa gcttgccacg gttgctcctg agcacacggt gttcgctacc | 360 |
| aactcctcga cgctgctgcc gagcgatctc aaggagttca ccggccgtcc cgagaagttc | 420 |
| ctcgcactgc acttcgcaaa tcacgtgtgg gtcaacaaca ctgccgaggt catgggcacc | 480 |
| gagtccaccg accccgccgt gtaccgcgag gtcgtcgagt tcgcgaagaa catcggcatg | 540 |
| gtgccgatcg aactcaagaa ggagaaggcg ggctacgtac tcaactcgct cctggtcccg | 600 |
| ctcctcaacg cggcctccga cctgctgatc gacggcatcg ccgatcccga catggtcgac | 660 |
| aagacgtggc gtatcggcac cggagccccg tggggcccct tccagatcat ggacgtcgtc | 720 |
| gggttgacca ccgtctacaa catctcctcc cagggcggcg agaagcagcg cgaattcgcc | 780 |
| gactacatca gaagaactg catcgacgag ggcaagctcg gcgttgctgt cggcgacggc | 840 |
| ttctacaact acaagggctg a | 861 |

<210> SEQ ID NO 10
<211> LENGTH: 861
<212> TYPE: DNA
<213> ORGANISM: Artificial Sequence
<220> FEATURE:
<223> OTHER INFORMATION: Diketoreductase Mutant Coded Sequence
<220> FEATURE:
<221> NAME/KEY: misc_feature
<222> LOCATION: (282)..(282)
<223> OTHER INFORMATION: n=a, c, g or t

<400> SEQUENCE: 10

| | |
|---|---|
| atgactgaac tgaagcagat caccgttctg ggtaccggag ttctcggctc acagatcgcc | 60 |
| tatcagaccg cctgtcacgg tttcgacgtc gtcgcgtacg acatcaacgc cgaggtcatc | 120 |
| gaaaaggcca aggctcggtt cgactcgttg gccgcggcct acaaggccga aacgtcgag | 180 |
| ggtgccaagg aaggcaaggc tgacgaagcg ctgcaacgta ttacgtactc gtacgatcta | 240 |
| ggcgaagccg tcgccaaggc cgacctggtc atcgaggcag tncccgagga catcgccatc | 300 |
| aagcgcgaca cctacgagaa gcttgccacg gttgctcctg agcacacggt gttcgctacc | 360 |
| aactcctcga cgctgctgcc gagcgatctc aaggagttca ccggccgtcc cgagaagttc | 420 |
| ctcgcactgc acttcgcaaa tcacgtgtgg gtcaacaaca ctgccgaggt catgggcacc | 480 |
| gagtccaccg accccgccgt gtaccgcgag gtcgtcgagt tcgcgaagaa catcggcatg | 540 |
| gtgccgatcg aactcaagaa ggagaaggcg ggctacgtac tcaactcgct cctggtcccg | 600 |
| ctcctcaacg cggcctccga cctgctgatc gacggcatcg ccgatcccga catggtcgac | 660 |
| aagacgtggc gtatcggcac cggagccccg tggggcccct tccagatcat ggacgtcgtc | 720 |
| gggttgacca ccgtctacaa catctcctcc cagggcggcg agaagcagcg cgaattcgcc | 780 |

```
gactacatca agaagaacta catcgacgag ggcaagctcg gcgttgctgt cggcgacggc      840
ttctacaact acaagggctg a                                               861

<210> SEQ ID NO 11
<211> LENGTH: 861
<212> TYPE: DNA
<213> ORGANISM: Artificial Sequence
<220> FEATURE:
<223> OTHER INFORMATION: Diketoreductase Mutant Coded Sequence
<220> FEATURE:
<221> NAME/KEY: misc_feature
<222> LOCATION: (282)..(282)
<223> OTHER INFORMATION: n=a, c, g or t
<220> FEATURE:
<221> NAME/KEY: misc_feature
<222> LOCATION: (253)..(253)
<223> OTHER INFORMATION: r=g or a

<400> SEQUENCE: 11
atgactgaac tgaagcagat caccgttctg ggtaccggag ttctcggctc acagatcgcc       60
tatcagaccg cctgtcacgg tttcgacgtc gtcgcgtacg acatcaacgc cgaggtcatc      120
gaaaaggcca aggctcggtt cgactcgttg gccgcggcct acaaggccga gaacgtcgag      180
ggtgccaagg aaggcaaggc tgacgaagcg ctgcaacgta ttacgtactc gtacgatcta      240
ggcgaagccg tcgccaaggc cgacctggtc atcgaggcag tncccgagga catcgccatc      300
aagcgcgaca cctacgagaa gcttgccacg gttgctcctg agcacacggt gttcgctacc      360
aactcctcga cgctgctgcc gagcgatctc aaggagttca ccggccgtcc cgagaagttc      420
ctcgcactgc acttcgcaaa tcacgtgtgg caraacaaca ctgccgaggt catgggcacc      480
gagtccaccg accccgccgt gtaccgcgag gtcgtcgagt tcgcgaagaa catcggcatg      540
gtgccgatcg aactcaagaa ggagaaggcg ggctacgtac tcaactcgct cctggtcccg      600
ctcctcaacg cggcctccga cctgctgatc gacggcatcg ccgatcccga catggtcgac      660
aagacgtggc gtatcggcac cggagccccg tggggcccct tccagatcat ggacgtcgtc      720
gggttgacca ccgtctacaa catctcctcc cagggcggcg agaagcagcg cgaattcgcc      780
gactacatca agaagaacta catcgacgag ggcaagctcg gcgttgctgt cggcgacggc      840
ttctacaact acaagggctg a                                               861

<210> SEQ ID NO 12
<211> LENGTH: 861
<212> TYPE: DNA
<213> ORGANISM: Artificial Sequence
<220> FEATURE:
<223> OTHER INFORMATION: Diketoreductase Mutant Coded Sequence
<220> FEATURE:
<221> NAME/KEY: misc_feature
<222> LOCATION: (717)..(717)
<223> OTHER INFORMATION: h=a or c or t/u
<220> FEATURE:
<221> NAME/KEY: misc_feature
<222> LOCATION: (771)..(771)
<223> OTHER INFORMATION: r=g or a

<400> SEQUENCE: 12
atgactgaac tgaagcagat caccgttctg ggtaccggag ttctcggctc acagatcgcc       60
tatcagaccg cctgtcacgg tttcgacgtc gtcgcgtacg acatcaacgc cgaggtcatc      120
gaaaaggcca aggctcggtt cgactcgttg gccgcggcct acaaggccga gaacgtcgag      180
ggtgccaagg aaggcaaggc tgacgaagcg ctgcaacgta ttacgtactc gtacgatcta      240
```

```
ggcgaagccg tcgccaaggc cgacctggtc atcgaggcaa ttcccgagga catcgccatc      300
aagcgcgaca cctacgagaa gcttgccacg gttgctcctg agcacacggt gttcgctacc      360
aactcctcga cgctgctgcc gagcgatctc aaggagttca ccggccgtcc cgagaagttc      420
ctcgcactgc acttcgcaaa tcacgtgtgg gtcaacaaca ctgccgaggt catgggcacc      480
gagtccaccg accccgccgt gtaccgcgag gtcgtcgagt tcgcgaagaa catcggcatg      540
gtgccgatcg aactcaagaa ggagaaggcg ggctacgtac tcaactcgct cctggtcccg      600
ctcctcaacg cggcctccga cctgctgatc gacggcatcg ccgatcccga catggtcgac      660
aagacgtggc gtatcggcac cggagccccg ttcggcccct tccagatcat ggacathgtc      720
gggttgacca ccgtctacaa catctcctcc cagggcggcg agaagcagaa rgaattcgcc      780
gactacatca agaagaacta catcgacgag ggcaagctcg gcgttgctgt cggcgacggc      840
ttctacaact acaagggctg a                                                861
```

<210> SEQ ID NO 13
<211> LENGTH: 861
<212> TYPE: DNA
<213> ORGANISM: Artificial Sequence
<220> FEATURE:
<223> OTHER INFORMATION: Diketoreductase Mutant Coded Sequence
<220> FEATURE:
<221> NAME/KEY: misc_feature
<222> LOCATION: (453,771)
<223> OTHER INFORMATION: r=g or a

<400> SEQUENCE: 13

```
atgactgaac tgaagcagat caccgttctg ggtaccggag ttctcggctc acagatcgcc       60
tatcagaccg cctgtcacgg tttcgacgtc gtcgcgtacg acatcaacgc cgaggtcatc      120
gaaaaggcca aggctcggtt cgactcgttg gccgcggcct acaaggccga gaacgtcgag      180
ggtgccaagg aaggcaaggc tgacgaagcg ctgcaacgta ttacgtactc gtacgatcta      240
ggcgaagccg tcgccaaggc cgacctggtc atcgaggcaa ttcccgagga catcgccatc      300
aagcgcgaca cctacgagaa gcttgccacg gttgctcctg agcacacggt gttcgctacc      360
aactcctcga cgctgctgcc gagcgatctc aaggagttca ccggccgtcc cgagaagttc      420
ctcgcactgc acttcgcaaa tcacgtgtgg caraacaaca ctgccgaggt catgggcacc      480
gagtccaccg accccgccgt gtaccgcgag gtcgtcgagt tcgcgaagaa catcggcatg      540
gtgccgatcg aactcaagaa ggagaaggcg ggctacgtac tcaactcgct cctggtcccg      600
ctcctcaacg cggcctccga cctgctgatc gacggcatcg ccgatcccga catggtcgac      660
aagacgtggc gtatcggcac cggagccccg ttcggcccct tccagatcat ggacgtcgtc      720
gggttgacca ccgtctacaa catctcctcc cagggcggcg agaagcagaa rgaattcgcc      780
gactacatca agaagaacta catcgacgag ggcaagctcg gcgttgctgt cggcgacggc      840
ttctacaact acaagggctg a                                                861
```

<210> SEQ ID NO 14
<211> LENGTH: 861
<212> TYPE: DNA
<213> ORGANISM: Artificial Sequence
<220> FEATURE:
<223> OTHER INFORMATION: Diketoreductase Mutant Coded Sequence
<220> FEATURE:
<221> NAME/KEY: misc_feature
<222> LOCATION: (282)..(282)
<223> OTHER INFORMATION: n=a, c, g or t
<220> FEATURE:
<221> NAME/KEY: misc_feature
<222> LOCATION: (453)..(453)
<223> OTHER INFORMATION: r=g or a

<400> SEQUENCE: 14

```
atgactgaac tgaagcagat caccgttctg ggtaccggag ttctcggctc acagatcgcc    60
tatcagaccg cctgtcacgg tttcgacgtc gtcgcgtacg acatcaacgc cgaggtcatc   120
gaaaaggcca aggctcggtt cgactcgttg ccgcggcct acaaggccga aacgtcgag     180
ggtgccaagg aaggcaaggc tgacgaagcg ctgcaacgta ttacgtactc gtacgatcta   240
ggcgaagccg tcgccaaggc cgacctggtc atcgaggcag tncccgagga catcgccatc   300
aagcgcgaca cctacgagaa gcttgccacg gttgctcctg agcacacggt gttcgctacc   360
aactcctcga cgctgctgcc gagcgatctc aaggagttca ccggccgtcc cgagaagttc   420
ctcgcactgc acttcgcaaa tcacgtgtgg caraacaaca ctgccgaggt catgggcacc   480
gagtccaccg accccgccgt gtaccgcgag gtcgtcgagt tcgcgaagaa catcggcatg   540
gtgccgatcg aactcaagaa ggagaaggcg ggctacgtac tcaactcgct cctggtcccg   600
ctcctcaacg cggcctccga cctgctgatc gacggcatcg ccgatcccga catggtcgac   660
aagacgtggc gtatcggcac cggagccccg ttcggcccct tccagatcat ggacgtcgtc   720
gggttgacca ccgtctacaa catctcctcc cagggcggcg agaagcagcg cgaattcgcc   780
gactacatca agaagaacta catcgacgag ggcaagctcg cgttgctgt cggcgacggc    840
ttctacaact acaagggctg a                                             861
```

<210> SEQ ID NO 15
<211> LENGTH: 29
<212> TYPE: DNA
<213> ORGANISM: Artificial Sequence
<220> FEATURE:
<223> OTHER INFORMATION: Primer I94-Forward
<220> FEATURE:
<221> NAME/KEY: misc_feature
<222> LOCATION: (14)..(16)
<223> OTHER INFORMATION: n=a, t, g or c

<400> SEQUENCE: 15
ggtcatcgag gcannncccg aggacatcg                                      29

<210> SEQ ID NO 16
<211> LENGTH: 29
<212> TYPE: DNA
<213> ORGANISM: Artificial Sequence
<220> FEATURE:
<223> OTHER INFORMATION: Primer I94-Reverse
<220> FEATURE:
<221> NAME/KEY: misc_feature
<222> LOCATION: (14)..(16)
<223> OTHER INFORMATION: n=a, t, g or c

<400> SEQUENCE: 16
cgatgtcctc gggnnntgcc tcgatgacc                                      29

<210> SEQ ID NO 17
<211> LENGTH: 38
<212> TYPE: DNA
<213> ORGANISM: Artificial Sequence
<220> FEATURE:
<223> OTHER INFORMATION: Primer E96-Forward
<220> FEATURE:
<221> NAME/KEY: misc_feature
<222> LOCATION: (19)..(21)
<223> OTHER INFORMATION: n=a, t, g or c

<400> SEQUENCE: 17
gtcatcgagg caattcccnn ngacatcgcc atcaagcg                                38

<210> SEQ ID NO 18
<211> LENGTH: 38
<212> TYPE: DNA
<213> ORGANISM: Artificial Sequence
<220> FEATURE:
<223> OTHER INFORMATION: Primer E96-Reverse
<220> FEATURE:
<221> NAME/KEY: misc_feature
<222> LOCATION: (18)..(20)
<223> OTHER INFORMATION: n=a, t, g or c

<400> SEQUENCE: 18
cgcttgatgg cgatgtcnnn gggaattgcc tcgatgac                                38

<210> SEQ ID NO 19
<211> LENGTH: 40
<212> TYPE: DNA
<213> ORGANISM: Artificial Sequence
<220> FEATURE:
<223> OTHER INFORMATION: Primer R102-Forward
<220> FEATURE:
<221> NAME/KEY: misc_feature
<222> LOCATION: (19)..(21)
<223> OTHER INFORMATION: n=a, t, g or c

<400> SEQUENCE: 19
gaggacatcg ccatcaagnn ngacacctac gagaagcttg                              40

<210> SEQ ID NO 20
<211> LENGTH: 40
<212> TYPE: DNA
<213> ORGANISM: Artificial Sequence
<220> FEATURE:
<223> OTHER INFORMATION: Primer R102-Reverse
<220> FEATURE:
<221> NAME/KEY: misc_feature
<222> LOCATION: (20)..(22)
<223> OTHER INFORMATION: n=a, t, g or c

<400> SEQUENCE: 20
caagcttctc gtaggtgtcn nncttgatgg cgatgtcctc                              40

<210> SEQ ID NO 21
<211> LENGTH: 30
<212> TYPE: DNA
<213> ORGANISM: Artificial Sequence
<220> FEATURE:
<223> OTHER INFORMATION: Primer T124-Forward
<220> FEATURE:
<221> NAME/KEY: misc_feature
<222> LOCATION: (15)..(17)
<223> OTHER INFORMATION: n=a, t, g or c

<400> SEQUENCE: 21
ctaccaactc ctcgnnnctg ctgccgagcg                                         30

<210> SEQ ID NO 22
<211> LENGTH: 30
<212> TYPE: DNA
<213> ORGANISM: Artificial Sequence
<220> FEATURE:
<223> OTHER INFORMATION: Primer T124-Reverse
<220> FEATURE:
<221> NAME/KEY: misc_feature
<222> LOCATION: (14)..(16)
<223> OTHER INFORMATION: n=a, t, g or c

```
<400> SEQUENCE: 22
cgctcggcag cagnnncgag gagttggtag                                     30

<210> SEQ ID NO 23
<211> LENGTH: 30
<212> TYPE: DNA
<213> ORGANISM: Artificial Sequence
<220> FEATURE:
<223> OTHER INFORMATION: Primer S123-Forward
<220> FEATURE:
<221> NAME/KEY: misc_feature
<222> LOCATION: (14)..(16)
<223> OTHER INFORMATION: n=a, t, g or c

<400> SEQUENCE: 23
cgctaccaac tccnnnacgc tgctgccgag                                     30

<210> SEQ ID NO 24
<211> LENGTH: 30
<212> TYPE: DNA
<213> ORGANISM: Artificial Sequence
<220> FEATURE:
<223> OTHER INFORMATION: Primer S123-Reverse
<220> FEATURE:
<221> NAME/KEY: misc_feature
<222> LOCATION: (15)..(17)
<223> OTHER INFORMATION: n=a, t, g or c

<400> SEQUENCE: 24
ctcggcagca gcgtnnngga gttggtagcg                                     30

<210> SEQ ID NO 25
<211> LENGTH: 27
<212> TYPE: DNA
<213> ORGANISM: Artificial Sequence
<220> FEATURE:
<223> OTHER INFORMATION: Primer H148-Forward
<220> FEATURE:
<221> NAME/KEY: misc_feature
<222> LOCATION: (13)..(15)
<223> OTHER INFORMATION: n=a, t, g or c

<400> SEQUENCE: 25
cacttcgcaa atnnngtgtg ggtcaac                                        27

<210> SEQ ID NO 26
<211> LENGTH: 28
<212> TYPE: DNA
<213> ORGANISM: Artificial Sequence
<220> FEATURE:
<223> OTHER INFORMATION: Primer H148-Reverse
<220> FEATURE:
<221> NAME/KEY: misc_feature
<222> LOCATION: (13)..(15)
<223> OTHER INFORMATION: n=a, t, g or c

<400> SEQUENCE: 26
gttgacccac acnnnatttg cgaagtgg                                       28

<210> SEQ ID NO 27
<211> LENGTH: 29
<212> TYPE: DNA
<213> ORGANISM: Artificial Sequence
<220> FEATURE:
<223> OTHER INFORMATION: Primer V151-Forward
<220> FEATURE:
<221> NAME/KEY: misc_feature
<222> LOCATION: (15)..(17)
```

```
<223> OTHER INFORMATION: n=a, t, g or c

<400> SEQUENCE: 27
caaatcacgt gtggnnnaac aacactgcc                                              29

<210> SEQ ID NO 28
<211> LENGTH: 29
<212> TYPE: DNA
<213> ORGANISM: Artificial Sequence
<220> FEATURE:
<223> OTHER INFORMATION: Primer V151-Reverse
<220> FEATURE:
<221> NAME/KEY: misc_feature
<222> LOCATION: (13)..(15)
<223> OTHER INFORMATION: n=a, t, g or c

<400> SEQUENCE: 28
ggcagtgttg ttnnnccaca cgtgatttg                                              29

<210> SEQ ID NO 29
<211> LENGTH: 29
<212> TYPE: DNA
<213> ORGANISM: Artificial Sequence
<220> FEATURE:
<223> OTHER INFORMATION: Primer E156-Forward
<220> FEATURE:
<221> NAME/KEY: misc_feature
<222> LOCATION: (14)..(16)
<223> OTHER INFORMATION: n=a, t, g or c

<400> SEQUENCE: 29
caacaacact gccnnngtca tgggcaccg                                              29

<210> SEQ ID NO 30
<211> LENGTH: 29
<212> TYPE: DNA
<213> ORGANISM: Artificial Sequence
<220> FEATURE:
<223> OTHER INFORMATION: Primer E156-Reverse
<220> FEATURE:
<221> NAME/KEY: misc_feature
<222> LOCATION: (14)..(16)
<223> OTHER INFORMATION: n=a, t, g or c

<400> SEQUENCE: 30
cggtgcccat gacnnnggca gtgttgttg                                              29

<210> SEQ ID NO 31
<211> LENGTH: 33
<212> TYPE: DNA
<213> ORGANISM: Artificial Sequence
<220> FEATURE:
<223> OTHER INFORMATION: Primer K189-Forward
<220> FEATURE:
<221> NAME/KEY: misc_feature
<222> LOCATION: (16)..(18)
<223> OTHER INFORMATION: n=a, t, g or c

<400> SEQUENCE: 31
gaactcaaga aggagnnngc gggctacgta ctc                                         33

<210> SEQ ID NO 32
<211> LENGTH: 33
<212> TYPE: DNA
<213> ORGANISM: Artificial Sequence
<220> FEATURE:
<223> OTHER INFORMATION: Primer K189-Reverse
<220> FEATURE:
<221> NAME/KEY: misc_feature
```

<222> LOCATION: (16)..(18)
<223> OTHER INFORMATION: n=a, t, g or c

<400> SEQUENCE: 32
gagtacgtag cccgcnnnct ccttcttgag ttc                                    33

<210> SEQ ID NO 33
<211> LENGTH: 40
<212> TYPE: DNA
<213> ORGANISM: Artificial Sequence
<220> FEATURE:
<223> OTHER INFORMATION: Primer G191-Forward
<220> FEATURE:
<221> NAME/KEY: misc_feature
<222> LOCATION: (22)..(24)
<223> OTHER INFORMATION: n=a, t, g or c

<400> SEQUENCE: 33
gaactcaaga aggagaaggc gnnntacgta ctcaactcgc                             40

<210> SEQ ID NO 34
<211> LENGTH: 40
<212> TYPE: DNA
<213> ORGANISM: Artificial Sequence
<220> FEATURE:
<223> OTHER INFORMATION: Primer G191-Reverse
<220> FEATURE:
<221> NAME/KEY: misc_feature
<222> LOCATION: (17)..(19)
<223> OTHER INFORMATION: n=a, t, g or c

<400> SEQUENCE: 34
gcgagttgag tacgtannnc gccttctcct tcttgagttc                             40

<210> SEQ ID NO 35
<211> LENGTH: 27
<212> TYPE: DNA
<213> ORGANISM: Artificial Sequence
<220> FEATURE:
<223> OTHER INFORMATION: Primer L194-Forward
<220> FEATURE:
<221> NAME/KEY: misc_feature
<222> LOCATION: (12)..(14)
<223> OTHER INFORMATION: n=a, t, g or c

<400> SEQUENCE: 35
cgggctacgt annnaactcg ctcctgg                                           27

<210> SEQ ID NO 36
<211> LENGTH: 27
<212> TYPE: DNA
<213> ORGANISM: Artificial Sequence
<220> FEATURE:
<223> OTHER INFORMATION: Primer L194-Reverse
<220> FEATURE:
<221> NAME/KEY: misc_feature
<222> LOCATION: (14)..(16)
<223> OTHER INFORMATION: n=a, t, g or c

<400> SEQUENCE: 36
ccaggagcga gttnnntacg tagcccg                                           27

<210> SEQ ID NO 37
<211> LENGTH: 30
<212> TYPE: DNA
<213> ORGANISM: Artificial Sequence
<220> FEATURE:
<223> OTHER INFORMATION: Primer W223-Forward
<220> FEATURE:

```
<221> NAME/KEY: misc_feature
<222> LOCATION: (14)..(16)
<223> OTHER INFORMATION: n=a, t, g or c

<400> SEQUENCE: 37
ggtcgacaag acgnnncgta tcggcaccgg                                30

<210> SEQ ID NO 38
<211> LENGTH: 30
<212> TYPE: DNA
<213> ORGANISM: Artificial Sequence
<220> FEATURE:
<223> OTHER INFORMATION: Primer W223-Reverse
<220> FEATURE:
<221> NAME/KEY: misc_feature
<222> LOCATION: (15)..(17)
<223> OTHER INFORMATION: n=a, t, g or c

<400> SEQUENCE: 38
ccggtgccga tacgnnncgt cttgtcgacc                                30

<210> SEQ ID NO 39
<211> LENGTH: 40
<212> TYPE: DNA
<213> ORGANISM: Artificial Sequence
<220> FEATURE:
<223> OTHER INFORMATION: Primer F231-Forward
<220> FEATURE:
<221> NAME/KEY: misc_feature
<222> LOCATION: (20)..(22)
<223> OTHER INFORMATION: n=a, t, g or c

<400> SEQUENCE: 39
tatcggcacc ggagccccgn nnggcccctt ccagatcatg                     40

<210> SEQ ID NO 40
<211> LENGTH: 40
<212> TYPE: DNA
<213> ORGANISM: Artificial Sequence
<220> FEATURE:
<223> OTHER INFORMATION: Primer F231-Reverse
<220> FEATURE:
<221> NAME/KEY: misc_feature
<222> LOCATION: (19)..(21)
<223> OTHER INFORMATION: n=a, t, g or c

<400> SEQUENCE: 40
catgatctgg aaggggccnn ncggggctcc ggtgccgata                     40

<210> SEQ ID NO 41
<211> LENGTH: 32
<212> TYPE: DNA
<213> ORGANISM: Artificial Sequence
<220> FEATURE:
<223> OTHER INFORMATION: Primer M237-Forward
<220> FEATURE:
<221> NAME/KEY: misc_feature
<222> LOCATION: (15)..(17)
<223> OTHER INFORMATION: n=a, t, g or c

<400> SEQUENCE: 41
gccccttcca gatcnnngac gtcgtcgggt tg                             32

<210> SEQ ID NO 42
<211> LENGTH: 32
<212> TYPE: DNA
<213> ORGANISM: Artificial Sequence
<220> FEATURE:
<223> OTHER INFORMATION: Primer M237-Reverse
```

```
<220> FEATURE:
<221> NAME/KEY: misc_feature
<222> LOCATION: (16)..(18)
<223> OTHER INFORMATION: n=a, t, g or c

<400> SEQUENCE: 42
caacccgacg acgtcnnnga tctggaaggg gc                                  32

<210> SEQ ID NO 43
<211> LENGTH: 33
<212> TYPE: DNA
<213> ORGANISM: Artificial Sequence
<220> FEATURE:
<223> OTHER INFORMATION: Primer V239-Forward
<220> FEATURE:
<221> NAME/KEY: misc_feature
<222> LOCATION: (17)..(19)
<223> OTHER INFORMATION: n=a, t, g or c

<400> SEQUENCE: 43
cttccagatc atggacnnng tcggttgac cac                                  33

<210> SEQ ID NO 44
<211> LENGTH: 33
<212> TYPE: DNA
<213> ORGANISM: Artificial Sequence
<220> FEATURE:
<223> OTHER INFORMATION: Primer V239-Reverse
<220> FEATURE:
<221> NAME/KEY: misc_feature
<222> LOCATION: (15)..(17)
<223> OTHER INFORMATION: n=a, t, g or c

<400> SEQUENCE: 44
gtggtcaacc cgacnnngtc catgatctgg aag                                 33

<210> SEQ ID NO 45
<211> LENGTH: 27
<212> TYPE: DNA
<213> ORGANISM: Artificial Sequence
<220> FEATURE:
<223> OTHER INFORMATION: Primer V240-Forward
<220> FEATURE:
<221> NAME/KEY: misc_feature
<222> LOCATION: (14)..(16)
<223> OTHER INFORMATION: n=a, t, g or c

<400> SEQUENCE: 45
gatcatggac gtcnnngggt tgaccac                                        27

<210> SEQ ID NO 46
<211> LENGTH: 27
<212> TYPE: DNA
<213> ORGANISM: Artificial Sequence
<220> FEATURE:
<223> OTHER INFORMATION: Primer V240-Reverse
<220> FEATURE:
<221> NAME/KEY: misc_feature
<222> LOCATION: (12)..(14)
<223> OTHER INFORMATION: n=a, t, g or c

<400> SEQUENCE: 46
gtggtcaacc cnnngacgtc catgatc                                        27

<210> SEQ ID NO 47
<211> LENGTH: 29
<212> TYPE: DNA
<213> ORGANISM: Artificial Sequence
<220> FEATURE:
```

<223> OTHER INFORMATION: Primer N247-Forward
<220> FEATURE:
<221> NAME/KEY: misc_feature
<222> LOCATION: (14)..(16)
<223> OTHER INFORMATION: n=a, t, g or c

<400> SEQUENCE: 47
gaccaccgtc tacnnnatct cctcccagg                                29

<210> SEQ ID NO 48
<211> LENGTH: 29
<212> TYPE: DNA
<213> ORGANISM: Artificial Sequence
<220> FEATURE:
<223> OTHER INFORMATION: Primer N247-Reverse
<220> FEATURE:
<221> NAME/KEY: misc_feature
<222> LOCATION: (14)..(16)
<223> OTHER INFORMATION: n=a, t, g or c

<400> SEQUENCE: 48
cctgggagga gatnnngtag acggtggtc                                29

<210> SEQ ID NO 49
<211> LENGTH: 29
<212> TYPE: DNA
<213> ORGANISM: Artificial Sequence
<220> FEATURE:
<223> OTHER INFORMATION: Primer Q251-Forward
<220> FEATURE:
<221> NAME/KEY: misc_feature
<222> LOCATION: (14)..(16)
<223> OTHER INFORMATION: n=a, t, g or c

<400> SEQUENCE: 49
caacatctcc tccnnnggcg gcgagaagc                                29

<210> SEQ ID NO 50
<211> LENGTH: 29
<212> TYPE: DNA
<213> ORGANISM: Artificial Sequence
<220> FEATURE:
<223> OTHER INFORMATION: Primer Q251-Reverse
<220> FEATURE:
<221> NAME/KEY: misc_feature
<222> LOCATION: (14)..(16)
<223> OTHER INFORMATION: n=a, t, g or c

<400> SEQUENCE: 50
gcttctcgcc gccnnnggag gagatgttg                                29

<210> SEQ ID NO 51
<211> LENGTH: 44
<212> TYPE: DNA
<213> ORGANISM: Artificial Sequence
<220> FEATURE:
<223> OTHER INFORMATION: Primer R257-Forward
<220> FEATURE:
<221> NAME/KEY: misc_feature
<222> LOCATION: (21)..(23)
<223> OTHER INFORMATION: n=a, t, g or c

<400> SEQUENCE: 51
cccagggcgg cgagaagcag nnngaattcg ccgactacat caag               44

<210> SEQ ID NO 52
<211> LENGTH: 44
<212> TYPE: DNA
<213> ORGANISM: Artificial Sequence

```
<220> FEATURE:
<223> OTHER INFORMATION: Primer R257-Reverse
<220> FEATURE:
<221> NAME/KEY: misc_feature
<222> LOCATION: (22)..(24)
<223> OTHER INFORMATION: n=a, t, g or c

<400> SEQUENCE: 52
cttgatgtag tcggcgaatt cnnnctgctt ctcgccgccc tggg         44

<210> SEQ ID NO 53
<211> LENGTH: 31
<212> TYPE: DNA
<213> ORGANISM: Artificial Sequence
<220> FEATURE:
<223> OTHER INFORMATION: Primer L273-Forward
<220> FEATURE:
<221> NAME/KEY: misc_feature
<222> LOCATION: (17)..(19)
<223> OTHER INFORMATION: n=a, t, g or c

<400> SEQUENCE: 53
catcgacgag ggcaagnnng gcgttgctgt c         31

<210> SEQ ID NO 54
<211> LENGTH: 31
<212> TYPE: DNA
<213> ORGANISM: Artificial Sequence
<220> FEATURE:
<223> OTHER INFORMATION: Primer L273-Reverse
<220> FEATURE:
<221> NAME/KEY: misc_feature
<222> LOCATION: (13)..(15)
<223> OTHER INFORMATION: n=a, t, g or c

<400> SEQUENCE: 54
gacagcaacg ccnnncttgc cctcgtcgat g         31

<210> SEQ ID NO 55
<211> LENGTH: 40
<212> TYPE: DNA
<213> ORGANISM: Artificial Sequence
<220> FEATURE:
<223> OTHER INFORMATION: Primer A276-Forward
<220> FEATURE:
<221> NAME/KEY: misc_feature
<222> LOCATION: (20)..(22)
<223> OTHER INFORMATION: n=a, t, g or c

<400> SEQUENCE: 55
cgagggcaag ctcggcgttn nngtcggcga cggcttctac         40

<210> SEQ ID NO 56
<211> LENGTH: 40
<212> TYPE: DNA
<213> ORGANISM: Artificial Sequence
<220> FEATURE:
<223> OTHER INFORMATION: Primer A276-Reverse
<220> FEATURE:
<221> NAME/KEY: misc_feature
<222> LOCATION: (19)..(21)
<223> OTHER INFORMATION: n=a, t, g or c

<400> SEQUENCE: 56
gtagaagccg tcgccgacnn naacgccgag cttgccctcg         40
```